(12) United States Patent
Nakatsuji et al.

(10) Patent No.: US 9,499,790 B2
(45) Date of Patent: *Nov. 22, 2016

(54) METHOD FOR PROMOTING DIFFERENTIATION OF PLURIPOTENT STEM CELLS INTO CARDIAC MUSCLE CELLS

(71) Applicant: Kyoto University, Kyoto-shi (JP)

(72) Inventors: Norio Nakatsuji, Kyoto (JP); Motonari Uesugi, Kyoto (JP); Kouhei Yamada, Kyoto (JP); Itsunari Minami, Kyoto (JP); Tomomi Otsuji, Kyoto (JP); Shinya Otsuka, Kyoto (JP)

(73) Assignee: KYOTO UNIVERSITY, Kyoto-shi (JP)

( * ) Notice: Subject to any disclaimer, the term of this patent is extended or adjusted under 35 U.S.C. 154(b) by 156 days.

This patent is subject to a terminal disclaimer.

(21) Appl. No.: 14/154,765

(22) Filed: Jan. 14, 2014

(65) Prior Publication Data

US 2014/0127807 A1     May 8, 2014

Related U.S. Application Data

(63) Continuation-in-part of application No. 13/777,765, filed on Feb. 26, 2013, now Pat. No. 8,658,425, which is a continuation of application No. PCT/JP2011/069054, filed on Aug. 24, 2011.

(30) Foreign Application Priority Data

Aug. 26, 2010  (JP) .................................. 2010-189548
Sep. 13, 2013  (JP) .................................. 2013-190462

(51) Int. Cl.
  *C07D 277/82*  (2006.01)
  *C12N 5/077*  (2010.01)
  *C07D 513/04*  (2006.01)

(52) U.S. Cl.
  CPC ........... *C12N 5/0657* (2013.01); *C07D 277/82* (2013.01); *C07D 513/04* (2013.01); *C12N 2501/415* (2013.01); *C12N 2501/999* (2013.01); *C12N 2506/02* (2013.01); *C12N 2506/45* (2013.01)

(58) Field of Classification Search
  USPC ....................................................... 548/163
  See application file for complete search history.

(56) References Cited

U.S. PATENT DOCUMENTS

| | | | |
|---|---|---|---|
| 4,970,318 A | 11/1990 | Schnur et al. | |
| 2003/0134859 A1 | 7/2003 | Amemiya et al. | |
| 2006/0276393 A1 | 12/2006 | Milburn et al. | |
| 2007/0134215 A1 | 6/2007 | Fukuda et al. | |
| 2007/0148185 A1 | 6/2007 | Rathore et al. | |
| 2007/0149466 A1 | 6/2007 | Milburn et al. | |
| 2009/0068742 A1 | 3/2009 | Yamanaka | |
| 2009/0170914 A1 | 7/2009 | Bornancin et al. | |
| 2010/0183565 A1 | 7/2010 | Laflamme et al. | |
| 2012/0244619 A1 | 9/2012 | Nakatsuji et al. | |
| 2013/0183753 A1 | 7/2013 | Nakatsuji et al. | |
| 2013/0274215 A1 | 10/2013 | Thies et al. | |
| 2014/0127807 A1 | 5/2014 | Nakatsuji et al. | |
| 2015/0017718 A1* | 1/2015 | Nakatsuji ............. | C07D 277/82 435/366 |
| 2016/0002600 A1 | 1/2016 | Nakatsuji et al. | |

FOREIGN PATENT DOCUMENTS

| | | |
|---|---|---|
| EP | 2014766 A1 | 1/2009 |
| JP | S63-190880 A | 8/1988 |
| JP | H02-017181 A | 1/1990 |
| JP | 2000-508919 A | 7/2000 |
| JP | 2001-510450 A | 7/2001 |
| JP | 2004-535199 A | 11/2004 |
| JP | 2005-330443 A | 12/2005 |
| JP | 2006-218035 A | 8/2006 |
| JP | 2007-252220 A | 10/2007 |
| JP | 2009-500357 A | 1/2009 |
| JP | 2009-531365 A | 9/2009 |
| WO | 97/41209 A1 | 11/1997 |
| WO | 98/17267 | 4/1998 |
| WO | 01/83427 A1 | 11/2001 |
| WO | 03/006950 A2 | 1/2003 |
| WO | 2005/037845 A1 | 4/2005 |
| WO | 2007/069666 A1 | 6/2007 |
| WO | WO-2007/070964 A1 | 6/2007 |
| WO | 2008/118820 A2 | 10/2008 |
| WO | 2009/006930 A1 | 1/2009 |
| WO | 2009/006997 A1 | 1/2009 |
| WO | 2009/007852 A2 | 1/2009 |
| WO | 2011/002950 A1 | 1/2011 |
| WO | 2011/071118 A1 | 6/2011 |
| WO | 2011/127164 A2 | 10/2011 |
| WO | 2012/026491 A1 | 3/2012 |
| WO | 2013/111875 A1 | 8/2013 |
| WO | 2014/136519 A1 | 9/2014 |

OTHER PUBLICATIONS

PubChem CID 2694580—National Center for Biotechnology Information. PubChem Compound Database; CID=2694580, http://pubchem.ncbi.nlm.nih.gov/summary/summary.cgi?cid=2694580 (accessed Dec. 21, 2015), create date Jul. 16, 2005.*

(Continued)

*Primary Examiner* — Laura L. Stockton

(74) *Attorney, Agent, or Firm* — Fox Rothschild LLP

(57) ABSTRACT

The present invention relates to a composition for promoting differentiation of pluripotent stem cells into cardiac muscle cells, and a method for inducing differentiation of pluripotent stem cells into cardiac muscle cells and a method for preparing cardiac muscle cells.

4 Claims, 23 Drawing Sheets

(56) References Cited

OTHER PUBLICATIONS

PubChem CID 2641096—National Center for Biotechnology Information. PubChem Compound Database; CID=2641096, http://pubchem.ncbi.nlm.nih.gov/summary/summary.cgi?cid=2641096 (accessed Dec. 21, 2015), create date Jul. 16, 2005.*
PubChem CID 1358256—National Center for Biotechnology Information. PubChem Compound Database; CID=1358256, http://pubchem.ncbi.nlm.nih.gov/summary/summary.cgi?cid=1358256 (accessed Dec. 21, 2015), create date Jul. 11, 2005.*
PubChem CID 1220560—National Center for Biotechnology Information. PubChem Compound Database; CID=1220560, http://pubchem.ncbi.nlm.nih.gov/summary/summary.cgi?cid=1220560 (accessed Dec. 21, 2015), create date Jul. 10, 2005.*
PubChem CID 8582409—National Center for Biotechnology Information. PubChem Compound Database; CID=8582409, http://pubchem.ncbi.nlm.nih.gov/summary/summary.cgi?cid=8582409 (accessed Dec. 21, 2015), create date Jul. 30, 2006.*
Graichen et al., "Enhanced cardiomyogenesis of human embryonic stem cells by a small molecular inhibitor of p38 MAPK", Differentiation (2008) 76:357-370.
Xu et al., "Chemically defined medium supporting cardiomyocyte differentiation of human embryonic stem cells", Differentiation (2008) 76:958-970.
Carlton et al., "Discovery of small molecule agonists of the bombesin receptor subtype 3 (BRS-3) based on an omeprazole lead", Bioorganic & Medicinal Chemistry Letters, 2008, vol. 18, No. 20, pp. 5451-5455.
Bellasio et al., "Substances with potential cardiovascular activity. 2-Acylaminobenzimidazoles with hypotensive activity", Farmaco, Edizione Scientifica, 1973, vol. 28, No. 2, pp. 164-182.
Harsanyi et al., "Reactions of acylcyanamides. I. New synthesis of 2-acylaminobenzoxazoles", Annali di Chimica (Rome, Italy), 1964, vol. 54, No. 11, pp. 1060-1065.
Database Registry [Online] : Chemical Abstracts Service, Columbus, Ohio, [retrieved on Oct. 7, 2011] Select Registry Numbers.
Yuasa et al., "Transient inhibition of BMP signaling by Noggin induces cardiomyocyte differentiation of mouse embryonic stem cell", Nature Biotechnology, 2005, vol. 23. No. 5, pp. 607-611.
Toyama, "ES Saibo×iPS Saibo kara no Shinkin Saibo Bunka×Seisei×Ishoku", Japanese Journal of Transplantation, 2009, vol. 44, No. 3, pp. 219-225.
Mummery et al., "Differentiation of Human Embryonic Stem Cells to Cardiomyocytes : Role of Coculture With Visceral Endoderm-Like Cells", Circulation, American Heart Association, 2003, 107, pp. 2733-2740.
Yang et al., "Human cardiovascular progenitor cells develop from a KDR1 embryonic-stem-cell-derived population, a KDR+ embryonic-stem-cell-derived population", Letter, Nature, 2008, vol. 453, pp. 524-529.
Leschik et al., "Cardiac commitment of primate embryonic stem cells", Nature Protocols, 2008, vol. 3, No. 9, pp. 1381-1387.
Stuckwisch et al., "Some N-Substituted Dimethoxyphenyl-acetamides and Dimethoxyphenylethylamines", Journal of Medicinal Chemistry, 1965, vol. 8, issue 5, pp. 734-735.
Thomson et al., "Embryonic Stem Cell Lines Derived from Human Blastocysts", Science, 1998, 282, pp. 1145-1147.
Suemori et al., "Efficient establishment of human embryonic stem cell lines and long-term maintenance with stable karyotype by enzymatic bulk passage", Biochemical and Biophysical Research Communications, 2006, 345, pp. 926-932.
Thomson et al., "Isolation of a primate embryonic stem cell line", Proc. Natl. Acad. Sci. USA, 1995, vol. 92, pp. 7844-7848.
Thomson et al., "Pluripotent Cell Lines Derived from Common Marmoset (Callithrix jacchus) Blastocysts1", Biology of Reproduction, 1996, 55, pp. 254-259.
Doetshman et al., "Establishment of Hamster Blastocyst-Derived Embryonic Stem (ES) Cells", Developmental Biology, 1988, 127. 224-227.

Evans et al., "Derivation and Preliminary Chabacterization of Pluripotent Cell Lines From Porcine and Bovine Blastocysts", Theriogenology, 1990, vol. 33, No. 1, pp. 125-128.
Piedrahita et al., "On the Isolation of Embryonic Stem Cells: Comparative Behavior of Murine, Porcine and Ovine Embryos", Theriogenology, 1990, vol. 34, No. 5, pp. 879-891.
Notarianni et al., "Maintenance and differentiation in culture of pluripotential embryonic cell lines from pig blastocysts", Journals of Reproduction & Fertility, 1990, 41, pp. 51-56.
Talbot et al., "Culturing the epiblast cells of the pig blastocyst", In Vitro Cell Dev. Biol., 1993, 29A, pp. 543-554Culturing the Epiblast Cells of the Pig Blastocyst.
Notarianni et al., "Derivation of pluripotent, embryonic cell lines from the pig and sheep", J. Reprod. Fert., 1991, 43, pp. 255-260.
Saito et al., "Bovine embryonic stem cell-like cell lines cultured over several passages", Roux's Arch Dev Biol, 1992, 201, pp. 134-141Bovine embryonic stem cell-like cell lines cultured over several passages.
Sukoyan et al. "Isolation and Cultivation of Blastocyst-Derived Stem Cell Lines From American Mink (*Muslela vision*)", Molecular Reproduction and Development, 1992, 33, pp. 418-431.
Shi et al., "Induction of Pluripotent Stem Cells from Mouse Embryonic Fibroblasts by Oct4 and Klf4 with Small-Molecule Compounds". Cell Stem Cell, 2008, 3, pp. 568-574
Zhou et al., "Generation of Induced Pluripotent Stem Cells Using Recombinant Proteins", Cell Stem Cell, 2009, 4, pp. 381-384.
Kim et al., "Pluripotent stem cells induced from adult neural stem cells by reprogramming with two factors", Nature, 2008, vol. 454, pp. 646-650.
Kim et al., "Oct4-Induced Pluripotency in Adult Neural Stem Cells", Cell, 2009, 136, pp. 411-419.
Huangfu et al., "Induction of pluripotent stem cells from primary human fibroblasts with only Oct4 and Sox2", Nature Biotechnology, 2008, vol. 26, pp. 1269-1275.
Zhao et al., "Two Supporting Factors Greatly Improve the Efficiency of Human iPSC Generation", Cell Stem Cell, 2008. 3, pp. 475-479.
Feng et al., "Reprogramming of fibroblasts into induced pluripotent stem cells with orphan nuclear receptor Esrrb", Nature Cell Biology, 2009, vol. 11, pp. 197-203.
Hanna et al., "Direct Reprogramming of Terminally Differentiated Mature B Lymphocytes to Pluripotency", Cell, 2008, 133, pp. 250-264.
Takahashi et al., "Induction of Pluripotent Stem Cells from Adult Human Fibroblasts by Defined Factors", Cell, 2007, 131, pp. 861-872.
Yu et al., "Cells Induced Pluripotent Stem Cell Lines Derived from Human Somatic", Science, 2007, 318, 1917-1920.
Shamblott et al., "Derivation of pluripotent stem cells from cultured human primordial germ cells", Proc. Natl. Acad. Sci. USA, 1998, vol. 95, pp. 13726-13731.
SciPlanner 2013, Chemical Abstracts Service, Columbus, OH; RN-349132-98-5.
SciPlanner 2013, Chemical Abstracts Service, Columbus, OH; RN-1118807-13-8.
STN Columbus search result of STN-Registry data base for "RN:308294-59-9", "RN:349132-90-7", "RN:805285-70-5", "RN:349438-98-8", "RN:953930-37-5", "RN:953995-50-1" and "RN:953993-61-8", access date Mar. 28, 2014.
Office Action dated Aug. 3, 2015 issued in U.S. Appl. No. 14/374,453.
Biechele et al, Porcupine homolog is required for canonical Wnt signaling and gastrulation in mouse embryos, Developmental Biology 355 (2011) 275-285.
Okita et al, Induced pluripotent stem cells: opportunities and challenges, Phil. Trans. R. Soc. B (2011) 366, 2198-2207.
Extended European Search Report dated Aug. 7, 2015 issued in European Patent Application No. 13740826.6.
Minami et al., "A Small Molecule that Promotes Cardiac Differentiation of Human Pluripotent Stem Cells under Defined, Cytokine- and Xeno-free Conditions", Cell Reports, vol. 2, No. 5, Nov. 29, 2012, pp. 1448-1460.

(56) References Cited

OTHER PUBLICATIONS

Asai, Y., Tada, M., Otsuji, T.G. & Nakatsuji, N. Combination of functional cardiomyocytes derived from human stem cells and a highly-efficient microelectrode array system: an ideal hybrid model assay for drug development. Curr Stem Cell Res Ther 5, 227-232 (2010).

Berge ten Derk, et al., "Embryonic stem cells require Wnt proteins to prevent differentiation to epiblast stem cells", Nature Cell Biol., 2011, vol. 13, No. 9, p. 1070-1075.

Burridge, P.W. et al. A universal system for highly efficient cardiac differentiation of human induced pluripotent stem cells that eliminates interline variability. PLoS One 6, e18293 (2011).

Chen, B. et al. Small molecule-mediated disruption of Wnt-dependent signaling in tissue regeneration and cancer. Nat Chem Biol 5, 100-107 (2009).

Chien, K.R., Domian, I.J. & Parker, K.K. Cardiogenesis and the complex biology of regenerative cardiovascular medicine. Science 322, 1494-1497 (2008).

Chien, K.R., Moretti, A. & Laugwitz, K.L. Development. ES cells to the rescue. Science 306, 239-240 (2004).

Even, M.S., Sandusky, C.B. & Barnard, N.D. Serum-free hybridoma culture: ethical, scientific and safety considerations. Trends Biotechnol 24, 105-108 (2006).

English Translation of IPRP dated Jul. 29, 2014 issued in corresponding International Application No. PCT/JP2013/051644.

English Translation of IPRP dated Mar. 19, 2013 issued in corresponding International Application No. PCT/JP2011/069054.

English Translation of ISR issued in corresponding International Application No. PCT/JP2013/051644 (2013).

Gonzalez Rodolfo, et al., "Stepwise Chemically Induced Cardiomyocyte Specification of Human Embryonic Stem Cells", Angew. Chem. Int. Ed., 2011, vol. 50, p. 11181-11185.

Gotea, V. & Ovcharenko, I. DiRE: identifying distant regulatory elements of co-expressed genes. Nucleic Acids Res 36, W133-139 (2008).

Hansson, E.M., Lindsay, M.E. & Chien, K.R. Regeneration next: toward heart stem cell therapeutics. Cell Stem Cell 5, 364-377 (2009).

Hao, J. et al. Dorsomorphin, a selective small molecule inhibitor of BMP signaling, promotes cardiomyogenesis in embryonic stem cells. PLoS One 3, e2904 (2008).

Ichida, J.K. et al. A small-molecule inhibitor of tgf-Beta signaling replaces sox2 in reprogramming by inducing nanog. Cell Stem Cell 5, 491-503 (2009).

Irion, S., Nostro, M.C., Kattman, S.J. & Keller, G.M. Directed differentiation of pluripotent stem cells: from developmental biology to therapeutic applications. Cold Spring Harb Symp Quant Biol 73, 101-110 (2008).

Jacot, J.G., Martin, J.C. & Hunt, D.L. Mechanobiology of cardiomyocyte development. J Biomech 43, 93-98 (2010).

Kamisuki, S. et al. A small molecule that blocks fat synthesis by inhibiting the activation of SREBP. Chem Biol 16, 882-892 (2009).

Kattman, S.J. et al. Stage-specific optimization of activin/nodal and BMP signaling promotes cardiac differentiation of mouse and human pluripotent stem cell lines. Cell Stem Cell 8, 228-240 (2011).

Laflamme, M.A. & Murry, C.E. Heart regeneration. Nature 473, 326-335 (2011).

Lluis Frederic, et al., "Periodic Activation of Wnt/?-Catenin Signaling Enhances Somatic Cell Reprogramming Mediated by Cell Fusion", Cell Stem Cell, 2008, Vol.3, p. 493-507.

Lutolf, M.P., Gilbert, P.M. & Blau, H.M. Designing materials to direct stem-cell fate. Nature 462, 433-441 (2009).

Menasche, P. Stem cell therapy for heart failure: are arrhythmias a real safety concern? Circulation 119, 2735-2740 (2009).

Mignone, J.L., Kreutziger, K.L., Paige, S.L. & Murry, C.E. Cardiogenesis from human embryonic stem cells. Circ J 74, 2517-2526 (2010).

Murakami, G. et al. Chemical library screening identifies a small molecule that downregulates SOD1 transcription for drugs to treat amyotrophic lateral sclerosis. J Biomol Screen 16, 405-414 (2011).

Naito, A.T. et al. Developmental stage-specific biphasic roles of Wnt/beta-catenin signaling in cardiomyogenesis and hematopoiesis. Proc Natl Acad Sci U S A 103, 19812-19817 (2006).

OA dated Apr. 29, 2014 issued in Chinese Patent Application 201180051572.7 along with its English translation.

Otsuji, T.G. et al. Progressive maturation in contracting cardiomyocytes derived from human embryonic stem cells: Qualitative effects on electrophysiological responses to drugs. Stem Cell Res 4, 201-213 (2010).

Paige, S.L. et al. Endogenous Wnt/beta-catenin signaling is required for cardiac differentiation in human embryonic stem cells. PLoS One 5, e11134 (2010).

Passier, R., van Laake, L.W. & Mummery, C.L. Stem-cell-based therapy and lessons from the heart. Nature 453, 322-329 (2008).

Qyang, Y. et al. The renewal and differentiation of Isl1+ cardiovascular progenitors are controlled by a Wnt/beta-catenin pathway. Cell Stem Cell 1, 165-179 (2007).

Rajala, K., Pekkanen-Mattila, M. & Aalto-Setala, K. Cardiac differentiation of pluripotent stem cells. Stem Cells Int 2011, 383709 (2011).

Ren, Y. et al. Small molecule Wnt inhibitors enhance the efficiency of BMP-4-directed cardiac differentiation of human pluripotent stem cells. J Mol Cell Cardiol 51, 280-287 (2011).

Sato, A., Kawazoe, Y., Kamisuki, S. & Uesugi, M. Synthesis of synthetic small molecule transcription factors (STF). Nucleic Acids Symp Ser (Oxf), 29-30 (2006).

Sato, S., Murata, A., Shirakawa, T. & Uesugi, M. Biochemical target isolation for novices: affinity-based strategies. Chem Biol 17, 616-623 (2010).

Segers, V.F. & Lee, R.T. Stem-cell therapy for cardiac disease. Nature 451, 937-942 (2008).

Smith, K. P. et al., Pluripotency: toward a gold standard for human ES and iPS cells, J Cell Physiol 220, 21-29 (2009).

Srivastava, D. & Ivey, K.N. Potential of stem-cell-based therapies for heart disease. Nature 441, 1097-1099 (2006).

STN Columbus search result of STN-Registry data base for RN:308294-59-9, RN:349132-90-7, 'RN:805285-70-5', RN:349438-98-8H, 'RN:953930-375', RN:953995-50-1 and RN:953993-61-8, access date Mar. 28, 2014.

Suemori, H. & Nakatsuji, N. Generation and characterization of monkey embryonic stem cells. Methods Mol Biol 329, 81-89 (2006).

Suemori, H. et al. Establishment of embryonic stem cell lines from cynomolgus monkey blastocysts produced by IVF or ICSI. Dev Dyn 222, 273-279 (2001).

Suessbrich, H., Waldegger, S., Lang, F. & Busch, A.E. Blockade of HERG channels expressed in Xenopus oocytes by the histamine receptor antagonists terfenadine and astemizole. FEBS Lett 385, 77-80 (1996).

Wada Keiki et al., "Hito Tanosei Kansaibo Kabu (ES Oyobi iPS Saibo Kabu) o Mochiita Bunka Yudo Gijutsu Oyobi HTS eno Oyo Tenkai", Medicine and Drug Journal, 2010, vol.46, S-1, pp. 247-253.

Wang, H., Hao, J. & Hong, C.C. Cardiac induction of embryonic stem cells by a small molecule inhibitor of Wnt/beta-catenin signaling. ACS Chem Biol 6, 192-197 (2011).

Willems, E. et al. Small-molecule inhibitors of the Wnt pathway potently promote cardiomyocytes from human embryonic stem cell-derived mesoderm. Circ Res 109, 360-364 (2011).

Xu, Y., Shi, Y. & Ding, S. A chemical approach to stem-cell biology and regenerative medicine. Nature 453, 338-344 (2008).

Yamashita, J.K. ES and iPS cell research for cardiovascular regeneration. Exp Cell Res 316, 2555-2559 (2010).

Yoshida, Y. & Yamanaka, S. iPS cells: a source of cardiac regeneration. J Mol Cell Cardiol 50, 327-332 (2011).

Zhu, W. et al. IGFBP-4 is an inhibitor of canonical Wnt signalling required for cardiogenesis. Nature 454, 345-349 (2008).

Lian, X., et al., "Robust cardiomyocyte differentiation from human pluripotent stem cells via temporal modulation of canonical Wnt signaling", Proc. Natl. Acad. Sci. USA 109, E1848-E1857, 2012.

International Search Report and Written Opinion dated Dec. 9, 2014 issued in International Application No. PCT/JP2014/074233.

English translation of International Preliminary Report on Patentability dated Mar. 15, 2016 issued in International Application No. PCT/JP2014/074233.

* cited by examiner

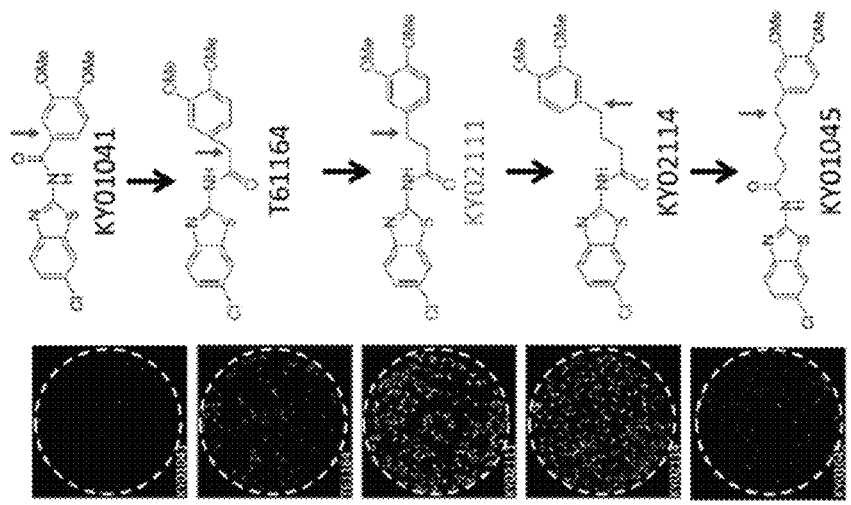
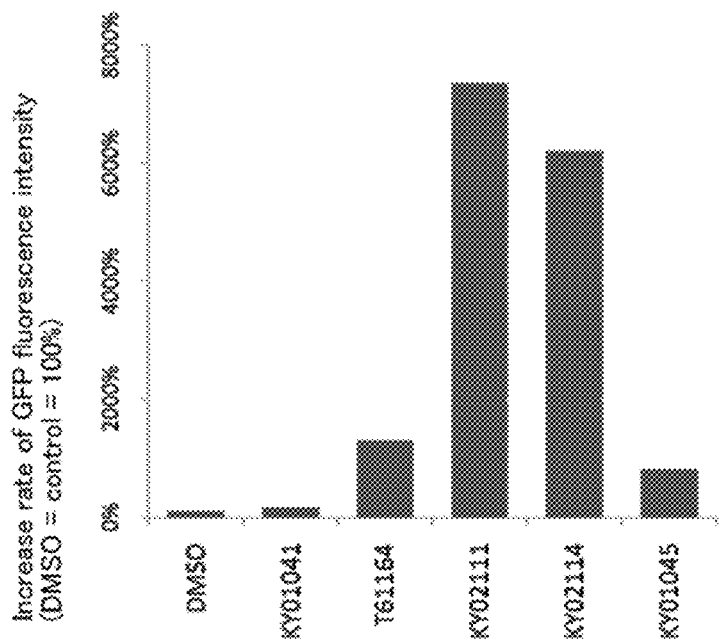
Fig. 3

List of active compounds

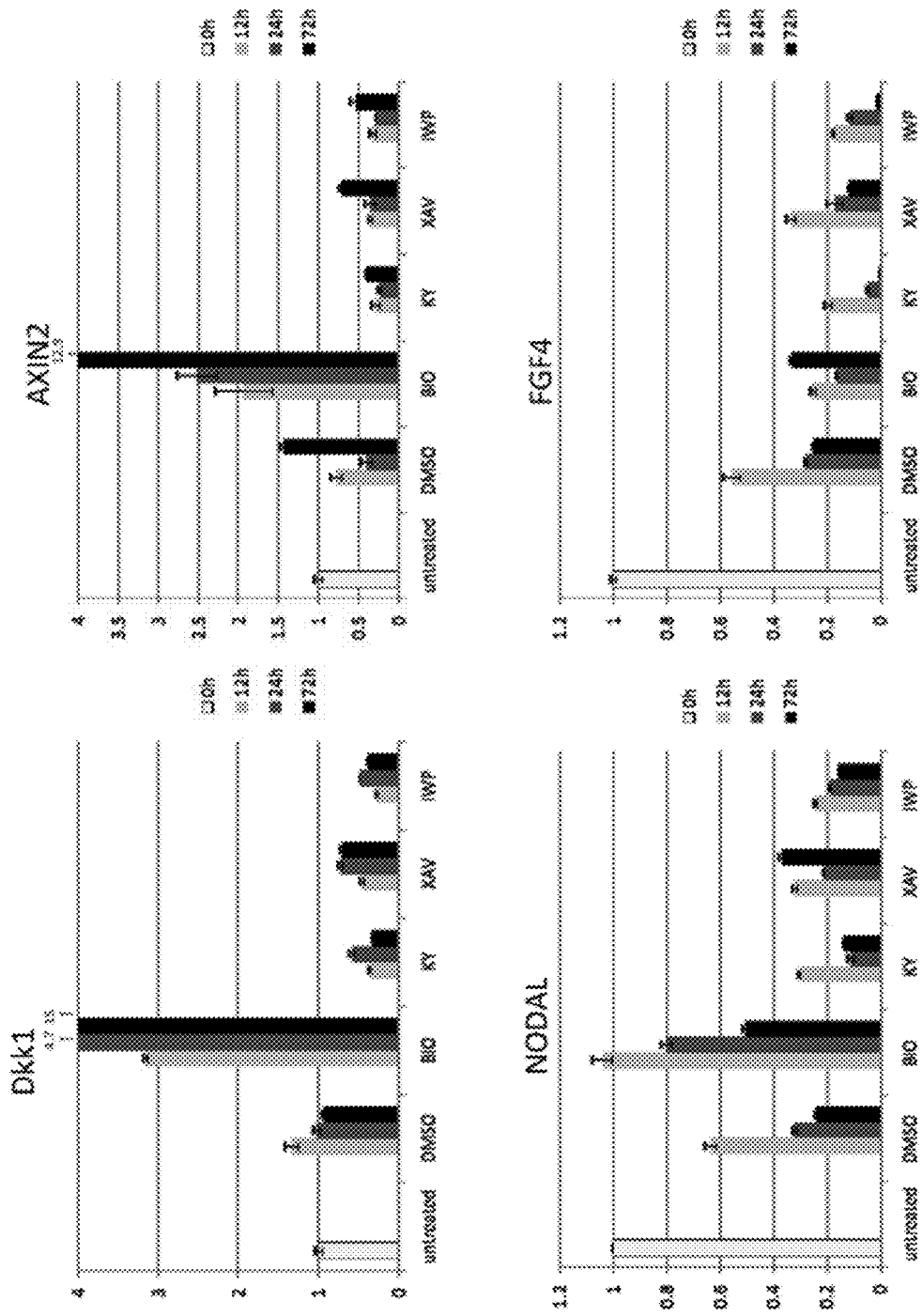

Cardiac muscle cells derived from monkey ES cells

Fig. 12
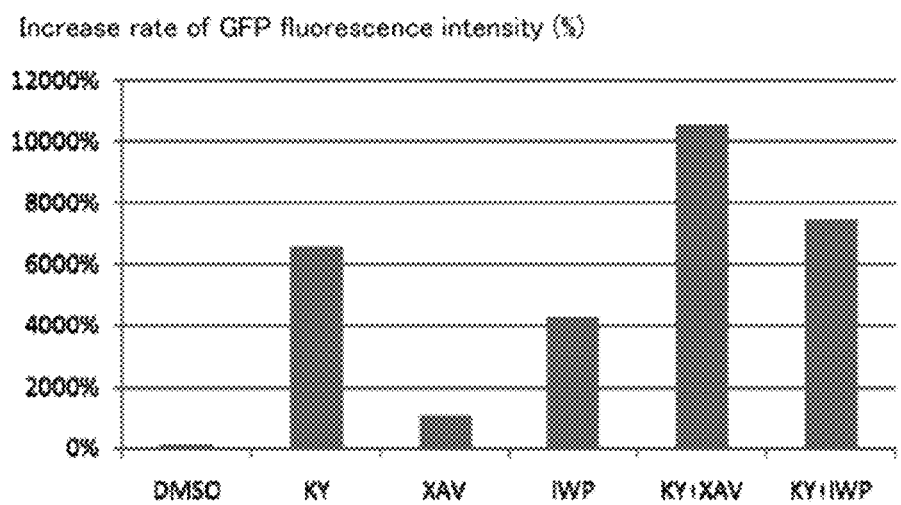
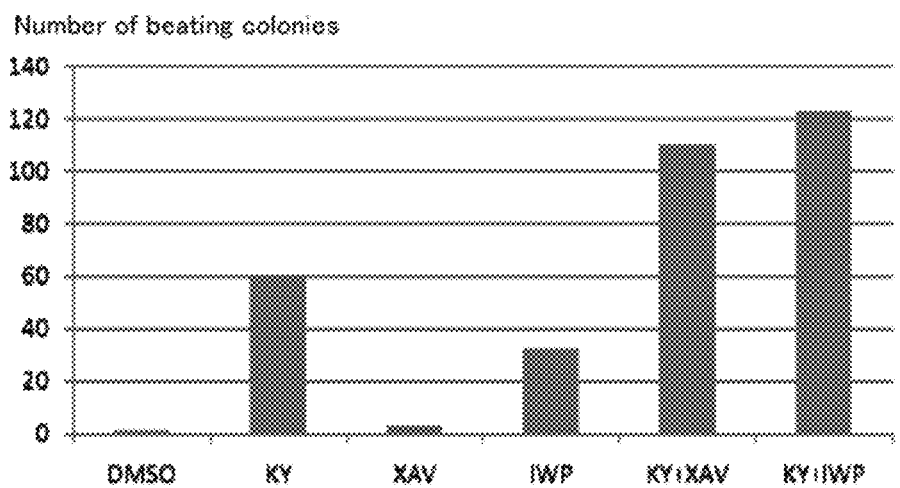

Fig. 17
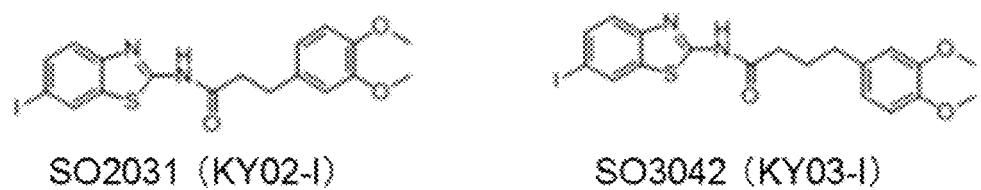
SO2031 (KY02-I)    SO3042 (KY03-I)
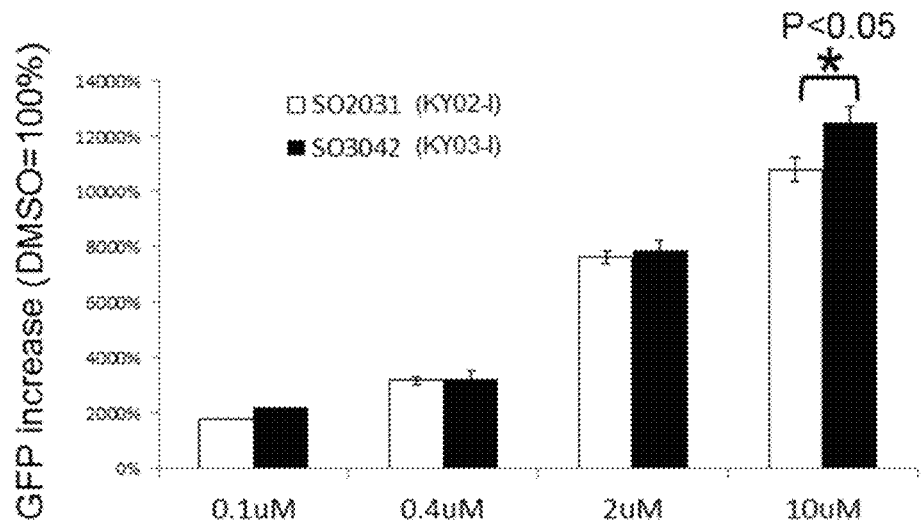

METHOD FOR PROMOTING DIFFERENTIATION OF PLURIPOTENT STEM CELLS INTO CARDIAC MUSCLE CELLS

CROSS-REFERENCE TO A RELATED APPLICATION

This application is a continuation-in-part of U.S. patent application Ser. No. 13/777,765 filed on Feb. 26, 2013, which is a continuation of International PCT Application No. PCT/JP2011/069054 filed on Aug. 24, 2011 that claims the benefit under 35 U.S.C. 119(d) of Japanese Patent Application No. 2010-189548 filed on Aug. 26, 2010. This application also claims the benefit under 35 U.S.C. 119(d) of Japanese Patent Application No. 2013-190462 filed on Sep. 13, 2013. The contents of the foregoing applications are hereby incorporated by reference in their entireties.

FIELD OF THE INVENTION

This invention relates to the field of regenerative medicine. In particular, the invention relates to a composition for promoting differentiation of pluripotent stem cells into cardiac muscle cells, where the composition contains iodobenzothiazolyl-phenyl-propanamide compounds. This invention also relates to a method for inducing differentiation of pluripotent stem cells into cardiac muscle cells.

BACKGROUND

A technology to induce differentiation of pluripotent stem cells holds the key for realization of regenerative medicine and establishment of in vitro drug screening study or evaluation of drug safety. In particular, it is important for the generative medicine and drug evaluation for heart diseases because heart diseases are currently the second cause of death in Japan. There are various drugs which induce severe side effects, including cardiac arrest and arrhythmia, leading to increasingly-demand to provide homogenous cardiac muscle cells which are useful for cardiotoxicity study. So far, it has been reported that cardiac muscle cell differentiation of human embryonic stem (ES) cells is induced by co-culturing human ES cells and mouse feeder cells, END2 cells (Mummery, C., et al., "Differentiation of human embryonic stem cells to cardiomyocytes: role of coculture with visceral endoderm-like cells." Circulation. 107(21), 2733-40 (2003); incorporated herein by reference in its entirety). However, differentiation efficiency of this method is not satisfactory and it is difficult to obtain pure human cardiac muscle cells since the resulting human cardiac muscle cells are often contaminated with mouse END2 cells. It is also reported that cardiac muscle cell differentiation is induced by preparing embryoid from ES cells and adding several cytokines (fibroblast growth factor (bFGF), bone morphogenetic protein 4 (BMP4), vascular endothelial cell growth factor (VEGF), Dickkopf-1 (DKK1), Activin A) to the embryoid (Yang, L., et al., "Human cardiovascular progenitor cells develop from a KDR+ embryonic-stem-cell-derived population," Nature, 453(7194), 524-8 (2008); Leschik, J., et al., "Cardiac commitment of primate embryonic stem cells." Nat. Protoc. 3(9), 1381-7 (2008); each incorporated herein by reference in its entirety). This method, however, requires a large amount of cytokines and can be rather expensive, while its differentiation efficiency is not enough.

There is therefore a continuing need in the fields of regenerative medicine and drug discovery to develop methods that can induce differentiation of pluripotent stem cells into cardiac muscle cells with high efficiency, minimal contamination and yet be cost-effective and suitable for commercial production.

SUMMARY

A novel composition is disclosed that can induce differentiation of pluripotent stem cells into cardiac muscle cells with high efficiency and low cost, which is demanded in the fields of regenerative medicine and drug discovery. The present invention provides a composition for promoting differentiation of pluripotent stem cells into cardiac muscle cells which comprises a compound represented by Formula (1) or a salt thereof:

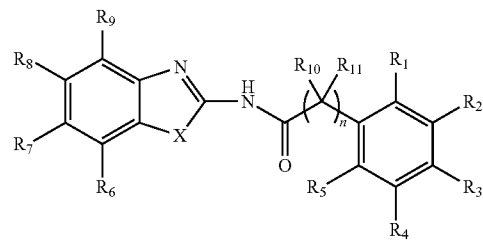

[1]

wherein $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group $—NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form $—O—CH_2—O—$ or $—O—(CH_2)_2—O—$, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group $—C(O)A$, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group $—NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form $—O—CH_2—O—$ or $—O—(CH_2)_2—O—$, $R_{10}$ to $R_{11}$ are each independently a hydrogen atom; or a linear or branched alkyl group having 1 to 5 carbon atoms, X is $—CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6.

In another embodiment, the present invention provides a method for inducing differentiation of pluripotent stem cells into cardiac muscle cells which comprises culturing pluripotent stem cells in a medium containing the composition for promoting differentiation of pluripotent stem cells into cardiac muscle cells as described above.

In another embodiment, the present invention provides a method for preparing cardiac muscle cells from pluripotent stem cells which comprises culturing pluripotent stem cells in a medium containing the composition for promoting differentiation of pluripotent stem cells into cardiac muscle cells as described above.

In yet another embodiment, the present invention provides a compound represented by Formula (1) or a salt thereof, wherein $R_1$, $R_4$ and $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom, $R_2$ and $R_3$ are a linear or a branched alkoxy group having 1 to 5 carbon atoms, or $R_2$ and $R_3$ join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—C— or —O—$(CH_2)_2$—O—, $R_{10}$ to $R_{11}$ are each independently a hydrogen atom; or a linear or branched alkyl group having 1 to 5 carbon atoms, X is an oxygen atom; a sulfur atom; or a group —$NR_{15}$, wherein $R_{15}$ is a hydrogen atom, a linear or branched alkyl group having 1 to 5 carbon atoms, or a linear or branched acyl group having 1 to 5 carbon atoms, n is an integer of 0 to 6, with the proviso that when n is 1 or 2, $R_7$ is not Cl nor a methoxy group, R2 is not a methoxy group.

In yet another embodiment, the present invention provides a compound represented by Formula (1) where $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, where two adjacent groups among $R_1$ to $R_5$ may join together to form —O—$CH_2$—O— or —O—$(CH_2)_2$—O—; $R_{12}$ and $R_{13}$ are each independently a hydrogen atom, an oxygen atom, or a linear or branched alkyl group having 1 to 5 carbon atoms which is unsubstituted or substituted with a halogen atom; $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$ wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, with the proviso that (i) when $R_1$, $R_4$, $R_5$, $R_6$, $R_8$, $R_9$, $R_{10}$ and $R_{11}$ are hydrogen atoms, $R_2$ and $R_3$ are methoxy groups, X is a sulfur atom and n is 1, then $R_7$ is not —$OCH_3$, —Cl or —$NO_2$, and (ii) when $R_1$, $R_4$, $R_5$, $R_6$, $R_8$, $R_9$, $R_{10}$ and $R_{11}$ are hydrogen atoms, $R_2$ and $R_3$ are methoxy groups, X is a sulfur atom and n is 2, then $R_7$ is not —Cl.

According to the present invention, it has become possible to induce differentiation of pluripotent stem cells into cardiac muscle cells without using feeder cells and obtain pure cardiac muscle cells. In addition, according to the present invention, it has become possible to induce cardiac muscle cell differentiation with higher efficiency at lower cost to prepare cardiac muscle cells than the known methods. The present invention is particularly useful for evaluation of QT prolongation which is critical for evaluation of drug safety in a high-throughput format, large-scale production of homogenous and mature human cardiac muscle cells for use in drug evaluation for heart diseases, and production of cardiac muscle cells for transplant to treat heart diseases, etc. Further, the composition of the present invention is not homologous in the molecular structure to the cardiac muscle cell differentiation promoters which have been reported so far, and the composition of the present invention is thus considered to be a totally new type of cardiac muscle cell differentiation promoter and expected to enhance the differentiation efficiency even more when used in combination with different cardiac muscle cell differentiation promoters.

These and other characteristics of the composition and a method of inducing differentiation of pluripotent stem cells into cardiac cells will become more apparent from the following description and illustrative embodiments which are described in detail with reference to the accompanying drawings. Similar elements in each figure are designated by like reference numbers and, hence, subsequent detailed descriptions thereof may be omitted for brevity.

BRIEF DESCRIPTION OF THE DRAWINGS

FIG. 3 illustrates the structure-activity relationship of KY02111 and analogous compounds thereof.

FIG. 5-1 illustrates the synergistic effect of promoting cardiac muscle cell differentiation between nitrovin and N11474.

FIG. 5-2 illustrates the synergistic effect of promoting cardiac muscle cell differentiation between nitrovin and KY02111.

FIG. 7-1 illustrates compounds which are effective in promoting cardiac muscle cell differentiation (1).

FIG. 7-2 illustrates the effect of promoting cardiac muscle cell differentiation of the respective compounds.

FIG. 9-1 illustrates the effects of Wnt signaling inhibitors and a Wnt signaling activator on gene expression (1).

FIG. 9-2 illustrates the effects of Wnt signaling inhibitors and a Wnt signaling activator on gene expression (2).

FIG. 11-1 illustrates the effects of a Wnt signaling activator on the effects of promoting cardiac muscle cell differentiation by KY02111, XAV939 and IWP2 (cardiac muscle cells derived from monkey ES cell).

FIG. 11-2 illustrates the effect of a Wnt signaling activator on the effect of promoting cardiac muscle cell differentiation by KY02111, XAV939, and IWP2 (human iPS cells).

FIG. 12 illustrates the synergistic effect between KY02111 and XAV939 or IWP2 in promoting cardiac muscle cell differentiation.

FIG. 17 is a plot of green fluorescent protein (GFP) expression increase (%) for SO2031 (KY02-I) and SO3042 (KY03-I) in a dose-dependent manner.

DETAILED DESCRIPTION

Figure 1:
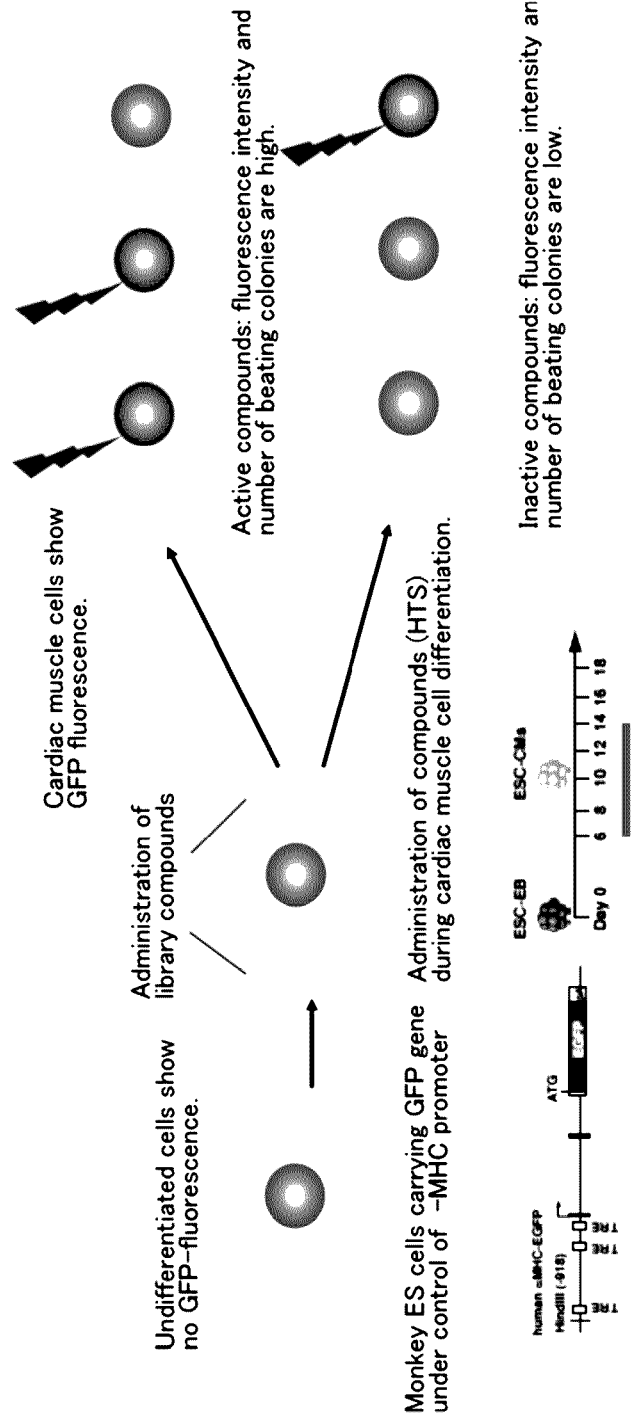
FIG. 1 illustrates a screening strategy of agents which promote cardiac muscle cell differentiation.

The present invention provides a composition for promoting differentiation of pluripotent stem cells into cardiac muscle cells containing a compound represented by Formula (1):

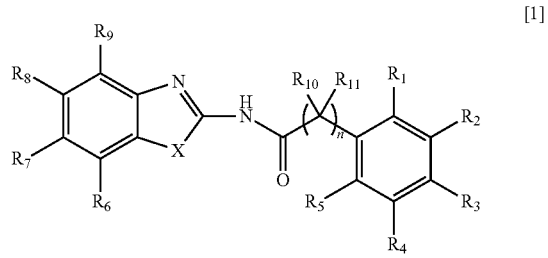

[1]

wherein $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among R1 to R5 may join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, or a salt thereof.

Examples of the linear or branched alkoxy group having 1 to 5 carbon atoms include a methoxy group, an ethoxy group, a propoxy group, an isopropoxy group, a butoxy group, an isobutoxy group, a sec-butoxy group, a tert-butoxy group and a pentyloxy group.

Examples of the linear or branched alkyl group having 1 to 5 carbon atoms include a methyl group, an ethyl group, a propyl group, an isopropyl group, a butyl group, an isobutyl group, a sec-butyl group, a tert-butyl group and a pentyl group.

Examples of the linear or branched acyl group having 1 to 5 carbon atoms include a formyl group, an acetyl group, a propionyl group, a butyryl group, an isobutyryl group, a valeryl group and an isovaleryl group.

Examples of the halogen atom include Cl, Br, I or F.

In a preferred embodiment, $R_1$ to $R_5$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; wherein two adjacent groups among R1 to R5 may join together to form —O—$CH_2$—O— or —O—$(CH_2)_2$—O—.

$R_2$ and $R_3$ are preferably a linear or a branched alkoxy group having 1 to 5 carbon atoms or join together to form —O—$CH_2$—O— or —O—$(CH_2)_2$—O—. Further preferably, $R_2$ and $R_3$ are a methoxy group, an ethoxy group or a propoxy group, and most preferably a methoxy group or an ethoxy group.

$R_1$, $R_4$ and $R_5$ are preferably a hydrogen atom.

In an embodiment, $R_6$ to $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_6$ and $R_9$ are preferably each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom, more preferably a hydrogen atom.

In a preferred embodiment, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; or $R_7$ and $R_8$ join together to form —O—$CH_2$—O— or —O—$(CH_2)_2$—C—.

In an embodiment, $R_7$ is a linear alkoxy group having 1 to 5 carbon atoms which is substituted with a group —C(O)A, and the group —C(O)A binds to the terminal carbon atom of the alkoxy group.

In a preferred embodiment, A contains at least one nitrogen atom, and examples of such A include a pyrrolidinyl, imidazol idinyl, pyrazolidinyl, pyrrolyl, imidazolyl, pyrazolyl, thiazolyl, isothiazolyl, oxazolyl, isooxazolyl, piperidinyl, piperazinyl, morpholinyl, pyridyl, pyrimidinyl, pyrazinyl and pyridazinyl groups which are unsubstituted or substituted with a linear or branched alkyl group having 1 to 5 carbon atoms. In a more preferred embodiment, A is a piperidinyl group, a piperazinyl group or a morpholinyl group which is unsubstituted or substituted with a linear or branched alkyl group having 1 to 5 carbon atoms. In a further preferred embodiment, A is a piperidin-1-yl group, a piperazin-1-yl group or a morpholin-4-yl group which is unsubstituted or substituted with a linear or branched alkyl group having 1 to 5 carbon atoms.

$R_{10}$ and $R_{11}$ are preferably a hydrogen atom.

In a preferred embodiment, X is an oxygen atom; a sulfur atom; or a group —$NR_{15}$, wherein $R_{15}$ is a hydrogen atom, a linear or branched alkyl group having 1 to 5 carbon atoms, a linear or branched acyl group having 1 to 5 carbon atoms. X is preferably a sulfur atom.

In a preferred embodiment, n is an integer of 0 to 4. In another preferred embodiment, n is an integer of 1 to 6, an integer of 1 to 4, or 2 or 3.

In a preferred embodiment, the composition of the present invention contains the compound or a salt thereof represented by Formula (32)

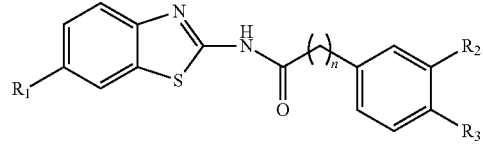

[32]

wherein $R_1$ is a halogen atom, preferably selected from I, Cl, or Br, and most preferably $R_1$ is I; $R_2$ and $R_3$ are each independently selected from a methoxy, an ethoxy, or a propoxy, with $R_2$ as a methoxy being preferred; and n is an integer of 1 to 4.

In a preferred embodiment, the composition of the present invention contains the compound selected from the following group or a salt thereof:

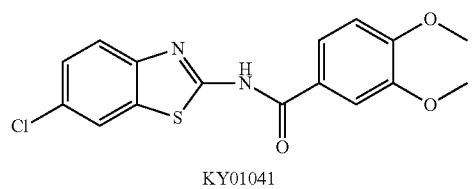
KY01041
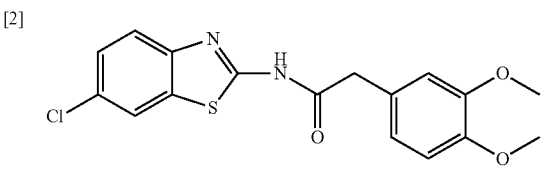
T61164
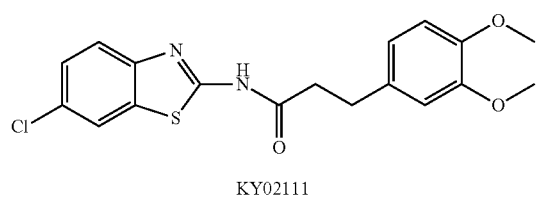
KY02111
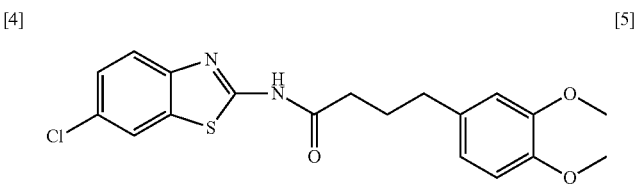
KY02114
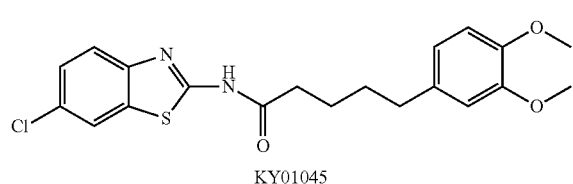
KY01045
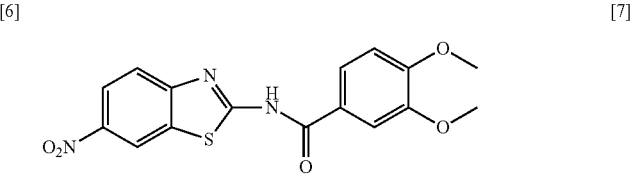
KY01040
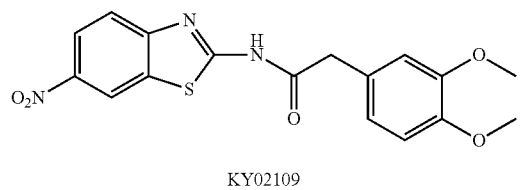
KY02109
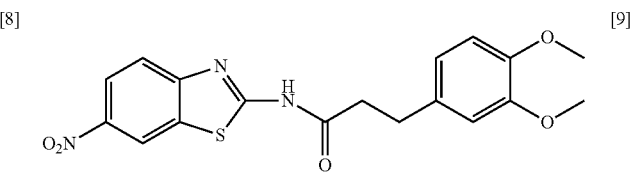
KY01042
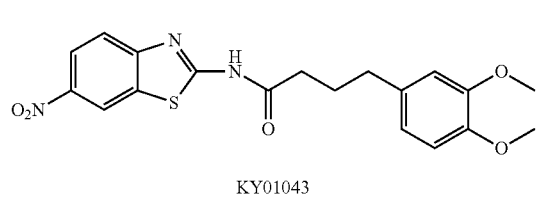
KY01043
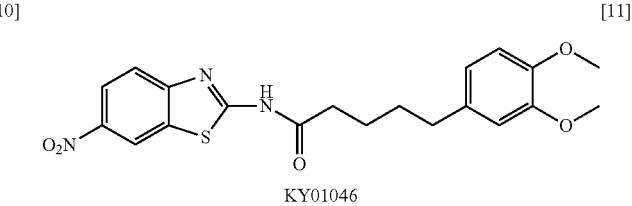
KY01046
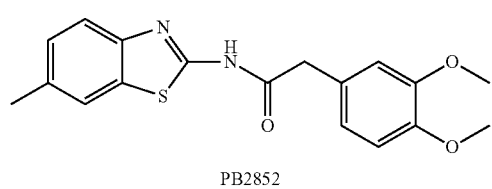
PB2852
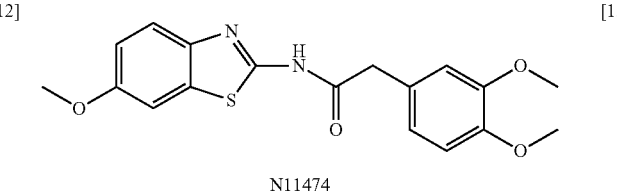
N11474
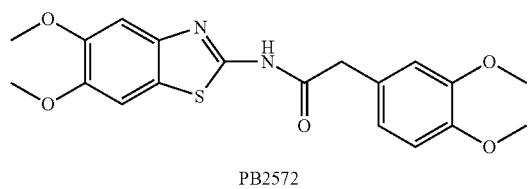
PB2572
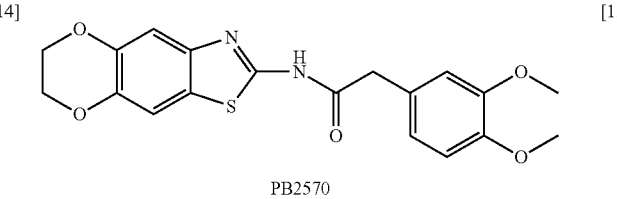
PB2570
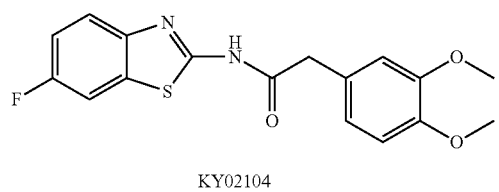
KY02104
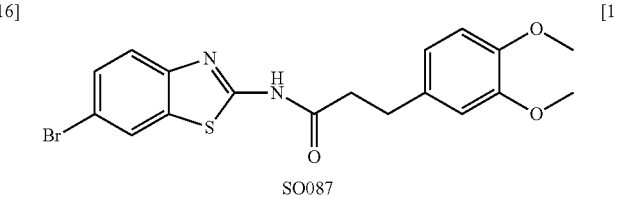
SO087

-continued
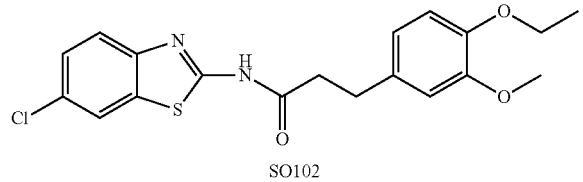
SO102
[18]
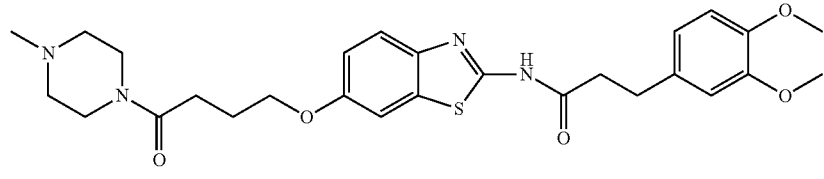
SO096
[19]
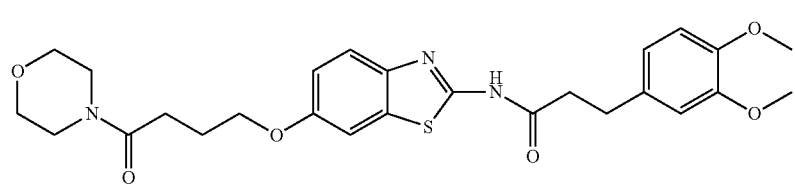
SO094
[20]
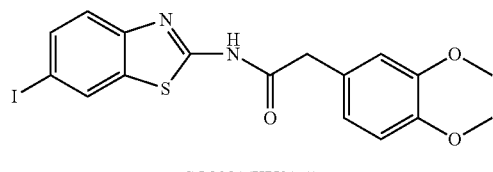
SO3031(KY01-1)
[21]
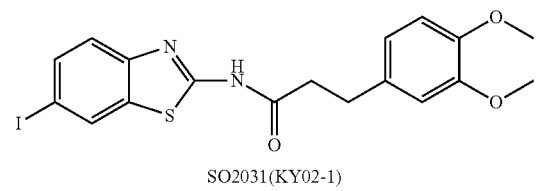
SO2031(KY02-1)
[22]
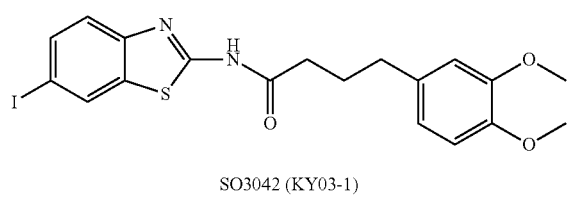
SO3042 (KY03-1)
[23]
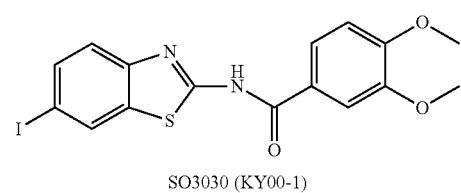
SO3030 (KY00-1)
[24]
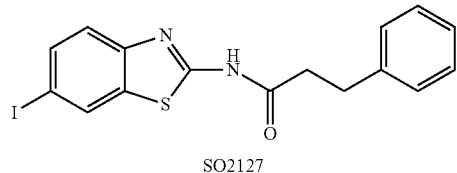
SO2127
[25]
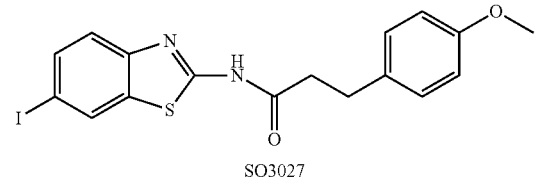
SO3027
[26]
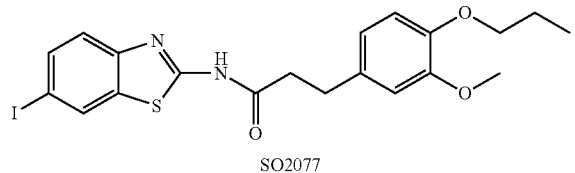
SO2077
[27]
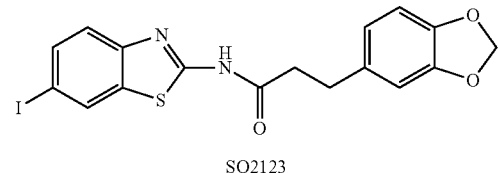
SO2123
[28]
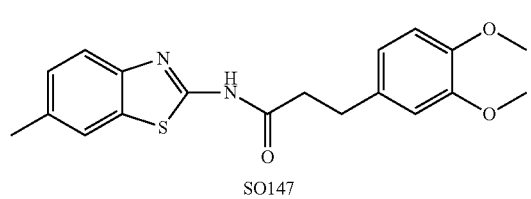
SO147
[29]
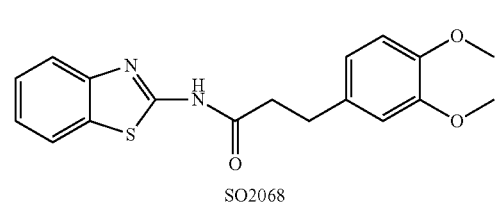
SO2068
[30]

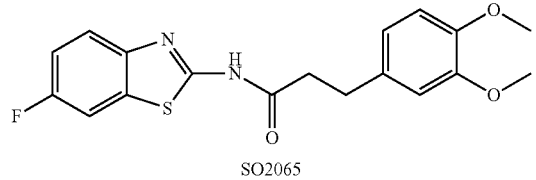
SO2065

Of the compounds listed above, the compounds with Formulae 5, 17, 18, 21, 22, 23, and 27 are being preferred.

The compounds of the present invention are described in, for example, *J. Med. Chem.*, 1965, 8 (5), pp 734-735 (incorporated herein by references in its entirety) (N11474, T61164). Also, they are available from UkrOrgSynthesis Ltd. (Kiev, Ukraine) (PB2852, PB2572, and PB2570) and Enamine LLC. (Monmouth, N.J.) (T61164), etc.

The compounds of the present invention can be synthesized by the known method (*J. Med. Chem.*, 1965, 8 (5), pp 734-735) or in accordance with the method described in Examples.

The term "pluripotent stem cells" herein used refers to cells having an ability to differentiate any type of cells constituting an adult body (pluripotency) and self-renewal capacity which is an ability to maintain the pluripotency during cell division. The "pluripotent stem cells" includes embryonic stem cells (ES cells), embryonic germ cells (EG cells), and induced pluripotent stem cell (iPS cells). The "pluripotent stem cells" may be cells of any species with no limitation, preferably mammalian cells, and more preferably rodent or primate cells. The present invention is particularly suitable for monkey or human pluripotent stem cells.

ES cells are pluripotent stem cells derived from early embryo and may be established from inner cell mass of a blastocyst or post-implantation epiblast in early embryo. Examples of ES cells include those described in the following references: human (Thomson J. A. et al., *Science* 282: 1145-1147 (1998), *Biochem Biophys Res Commun.* 345(3), 926-32 (2006); primates such as rhesus macaque and marmoset (Thomson J. A. et al., *Proc. Natl. Acad. Sci. USA* 92: 7844-7848 (1995); Thomson J. A. et al., *Biol. Reprod.* 55: 254-259 (1996)); rabbit (National Publication of International Patent Application No. 2000-508919); hamster (Doetshman T. et al., Dev. Biol. 127: 224-227 (1988)), hog (Evans M. J. et al., *Theriogenology* 33: 125128 (1990); Piedrahita J. A. et al., *Theriogenology* 34: 879-891 (1990); Notarianni E. et al., J. Reprod. Pert. 40: 51-56 (1990); Talbot N. C. et al., Cell. Dev. Biol. 29A: 546-554 (1993)), sheep (Notarianni E. et al., *J. Reprod. Fert. Suppl.* 43: 255-260 (1991)), cow (Evans M. J. et al., *Theriogenology* 33: 125-128 (1990); Saito S. et al., Roux. Arch. Dev. Biol. 201: 134-141 (1992)), and mink (Sukoyan M. A. et al., *Mol. Reorod. Dev.* 33: 418-431 (1993)) (these references are herein incorporated by reference).

EG cells are pluripotent stem cells derived from primordial germ cells, and examples include human EG cells (Shamblott, et al., *Proc. Natl. Acad. Sci. USA* 95: 13726-13731 (1998)) (the reference is herein incorporated by reference.)

The term "iPS cells" herein used refers to pluripotent stem cells induced from cells other than pluripotent stem cells such as somatic cells and tissue stem cells. Methods for preparing iPS cells are described in the following references, for example: WO2007/069666, WO2009/006930, WO2009/006997, WO2009/007852, WO2008/11.8820, *Cell Stem Cell* 3(5): 568-574 (2008), *Cell Stem Cell* 4(5): 381-384 (2009), *Nature* 454: 646-650 (2008), *Cell* 136(3): 411-419 (2009), *Nature Biotechnology* 26: 1269-1275 (2008), *Cell Stem Cell* 3: 475-479 (2008), *Nature Cell Biology* 11: 197-203 (2009), *Cell* 133(2): 250-264 (2008), *Cell* 131(5): 861-72 (2007), *Science* 318 (5858): 1917-20 (2007) (those references are herein incorporated by reference.) However, cells prepared by any method as long as they are pluripotent stem cells induced artificially are included in the "iPS cells" of the present invention.

The composition of the present invention may be added to a differentiation medium for cardiac muscle cells of pluripotent stem cells at a final concentration of the active ingredient of, for example, 0.5 to 20 μM. The differentiation medium for cardiac muscle cell may be any conventional medium used for cardiac muscle cell differentiation of pluripotent stem cells and the composition of the differentiation medium is not specifically limited. Examples of the differentiation medium include the IMDM-based differentiation medium for cardiac muscle cells (having the composition described below and used in the examples), DMEM-based differentiation medium for cardiac muscle cells (200 ml DMEM/F12 medium (Sigma) containing 50 ml bovine fetal serum (GIBCO), 2.5 ml MEM non-essential amino acid solution (Sigma), 2.5 ml penicillin-streptomycin (GIBCO), 200 mM L-glutamine, and 2.5 ml 2-mercaptoethanol), and StemPro-34SFM (GIBCO)+BMP4 (10 ng/ml). It is not necessary to use feeder cells such as END2 cells when the composition of the present invention is used. The composition of the present invention may be added at an appropriate time depending on the type of pluripotent stem cells and composition of the differentiation medium for cardiac muscle cell to be used. When monkey or human ES cells are cultured in the IMDM-based differentiation medium for cardiac muscle cells used in the examples, the composition of the present invention may be added to the differentiation medium for cardiac muscle cells during day 6 to 14 of culture.

The composition of the present invention may be used in combination with a different cardiac muscle cell differentiation promoter(s) such as nitrovin, cytokines (combination of bFGF, BMP4, VEGF, DKK1 and Activin A), or Wnt signaling inhibitors. The "cardiac muscle cell differentiation promoter" in the present invention include various substances effective in promoting cardiac muscle cell differentiation and thus, in this sense, the composition of the present invention is also one of the "cardiac muscle cell differentiation promoter". The "Wnt signaling inhibitor" in the present invention refers to a substance which inhibits the Wnt signaling pathway and examples include known compounds such as TWP2, XAV939, and IWR1, and proteins such as G-CSF, IGFBP4, and Dkk1. The composition of the present invention is also a useful "Wnt signaling inhibitor" in the present invention. More specifically, the embodiment, in which the composition of the present invention and a Wnt signaling inhibitor are used in combination, includes embodiments in which different types of the composition of the present invention are used. Preferably, the different cardiac muscle cell differentiation promoters used in combination are those having different action mechanism from the composition of the present invention, and examples of such promoters include IWP2 and XAV939. The administration schedule of the different cardiac muscle cell differentiation promoter may be determined as appropriate by those skilled in the art, depending on the agent to be used.

The present invention also provides a kit for promoting cardiac muscle cell differentiation containing the composition of the present invention. The kit of the present invention may contain a different cardiac muscle cell differentiation promoter(s) in addition to the composition of the present invention. The composition of the present invention and the different cardiac muscle cell differentiation promoter may be kept in separate containers or in a same container.

The present invention also provides a method for inducing cardiac muscle cell differentiation and a method for preparing cardiac muscle cells. The methods of the present invention are characterized in that pluripotent stem cells are cultured in a medium containing the composition of the present invention. In an embodiment, the method of the present invention comprises culturing pluripotent stem cells in a differentiation medium for cardiac muscle cells, adding the composition of the present invention to the differentiation medium such that the final concentration of the active ingredient is 0.5 to 20 μM during day 6 to 14 of culture and confirming differentiation of the pluripotent stem cells into cardiac muscle cells at day 18 of culture. In an another embodiment, the method of the present invention comprises culturing pluripotent stem cells in a differentiation medium for cardiac muscle cells, adding the composition of the present invention to the differentiation medium such that the final concentration of the active ingredient is 0.1 to 20 μM, preferably 0.1 to 10 μM, more preferably 0.4 to 10 μM, still more preferably 0.4 to 2 μM, most preferably 0.4 to 1 μM for 4-7 days during day 3 to 10 of culture (for example, day 4 to 8, day 4 to 9, day 4 to 10, day 3 to 8, day 3 to 9, or day 3 to 10 of culture), and after the culture with the composition of the invention, confirming differentiation of the pluripotent stem cells into cardiac muscle cells at day 8 or later, preferably at any day of day 8 to 14, more preferably at day 8, day 9, or day 10 of culture. Differentiation into cardiac muscle cells may be detected from the number of beating colonies of cardiac muscle cells or expression level of a marker of cardiac muscle cell differentiation such as α-MHC gene.

In the methods of the present invention, a different cardiac muscle cell differentiation promoter(s), in addition to the composition of the present invention, may further be added to a medium.

The cardiac muscle cells prepared by the method of the present invention may be used for evaluation of drug safety in vitro or as cardiac muscle cells as transplant to treat heart diseases.

The present invention also provides a compound having Formula (1) wherein $R_1$, $R_4$ and $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom, $R_2$ and $R_3$ are a linear or a branched alkoxy group having 1 to 5 carbon atoms, or $R_2$ and $R_3$ join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is an oxygen atom; a sulfur atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, with the proviso that when n is 1 or 2, $R_7$ is not Cl nor a methoxy group, $R_2$ is not a methoxy group, or a salt thereof.

In a preferred embodiment, $R_1$, $R_4$ and $R_5$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, preferably a hydrogen atom.

In a preferred embodiment, $R_2$ and $R_3$ are a methoxy group, an ethoxy group or a propoxy group.

In a preferred embodiment, $R_6$ and $R_9$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, preferably a hydrogen atom.

In a preferred embodiment, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; or $R_7$ and $R_8$ join together to form —O—$CH_2$—O— or —O—$(CH_2)_2$—O—.

In an embodiment, $R_7$ is a linear alkoxy group having 1 to 5 carbon atoms which is substituted with a group —C(O)A, and the group —C(O)A binds to the terminal carbon atom of the alkoxy group.

In a preferred embodiment, A contains at least one nitrogen atom and examples of such an A include a pyrrolidinyl, imidazolidinyl, pyrazolidinyl, pyrrolyl, imidazolyl, pyrazolyl, thiazolyl, isothiazolyl, oxazolyl, isooxazolyl, piperidinyl, piperazinyl, morpholinyl, pyridyl, pyrimidinyl, pyrazinyl and pyridazinyl group which are unsubstituted or substituted with a linear or branched alkyl group having 1 to 5 carbon atoms. In a more preferred embodiment, A is a piperidinyl group, a piperazinyl group or a morpholinyl group which is unsubstituted or substituted with a linear or branched alkyl group having 1 to 5 carbon atoms. In a further preferred embodiment, A is a piperidin-1-yl group, a piperazin-1-yl group or a morpholin-4-yl group which is unsubstituted or substituted with a linear or branched alkyl group having 1 to 5 carbon atoms.

In a preferred embodiment, $R_{10}$ and $R_{11}$ are a hydrogen atom.

In a preferred embodiment, X is a sulfur atom.

In a preferred embodiment, n is an integer of 0 to 4. In another preferred embodiment, n is an integer of 1 to 6, an integer of 1 to 4, or 2 or 3.

In a preferred embodiment, the compounds of the present invention have formulae 5 and 17-20.

In another preferred embodiment, the compounds of the present invention have formulae 21-28.

While the compositions that can induce differentiation of pluripotent stem cells into cardiac muscle cells have been described in connection with what is presently considered to be the most practical and preferred embodiment, it is to be understood that the invention is not to be limited to the disclosed embodiments, but on the contrary, is intended to cover various modifications and equivalent arrangements included within the spirit and scope of the appended claims.

EXAMPLES

The examples set forth below also serve to provide further appreciation of the invention but are not meant in any way to restrict the scope of the invention.

Example 1

Screening of Library Compounds

Figure 2:
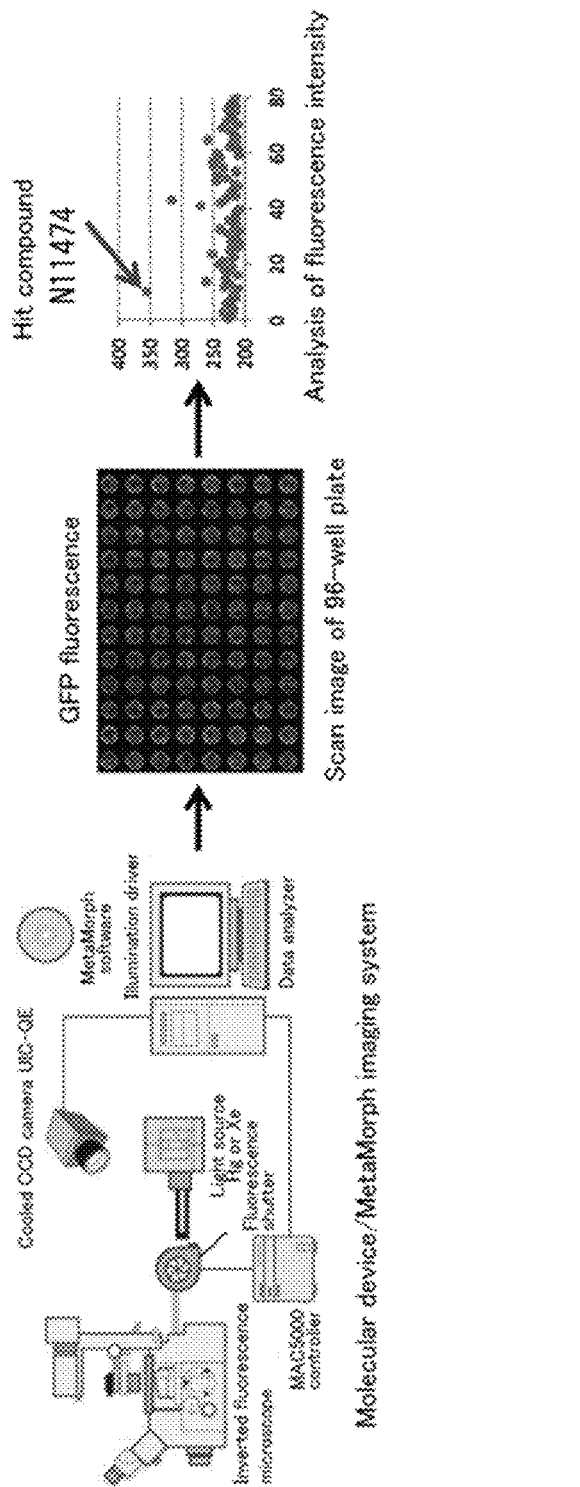
FIG. 2 illustrates a screening system and detection of N11474.

Screening of agents which promote cardiac muscle cell differentiation of monkey ES cells was performed as shown in FIG. 1. A vector expressing green fluorescent protein (GFP) under control of promoter of α-MHC gene, a marker of cardiac muscle cell differentiation, was introduced into monkey ES cell line (CMK 6.4 cynomolgus monkey ES cells) and the cells were seeded on 96-well culture plates (Greiner/655090: 96 well FIA black plate) in 5.0×103 cells/well, and cultured for 14 days in an IMDM-based differentiation medium for cardiac muscle cells (200 ml. IMDM (Sigma 13390) containing 50 ml bovine fetal serum (GIBCO 10099-141), 2.5 ml MEM non-essential amino acid solution (Sigma M7145), 2.5 ml penicillin-streptomycin (GIBCO 15140), 2.5 ml 200 mM L-glutamine, 2 µl 2-mercaptoethanol (Sigma M7522), 255 µl 5N NaOH). During day 6 to 14 of culture, 9,600 library compounds were added into separate wells (about 1 to 5 µM compound/well). Then, at day 1.4 of culture, GFP expression level was determined by using HCS (high contents screening) system (Molecular device/MetaMorph imaging system). As a result, the wells to which the low-molecular compound N11474 was added indicated high GFP expression levels, and N11474 was revealed to be effective in promoting cardiac muscle cell differentiation (FIG. 2).

Example 2

Structure-Activity Relationship of KY02111 and Other Analogues

KY02111, an analog of N11474 which was revealed to be effective in promoting cardiac muscle cell differentiation and analogous compounds thereof were synthesized and examined for the effect of promoting cardiac muscle cell differentiation. Monkey ES cells were seeded on a 6-well culture plate (Asahi Glass/5816-006: Ezview culture plate) in 4.0×105 cells/well, each compound was added thereto such that the final concentration thereof was 10 µM during day 4 to 10 of culture, and the GFP expression was observed at day 14 of culture. As a result, significant increases in the GFP expression level were found in accordance with the molecular structure of the compounds (FIG. 3). Also, the effect of promoting cardiac muscle cell differentiation was suggested to correlate with the length of a carbon chain binding to the dimethoxyphenyl group (FIG. 3).

Figures 1, 7:
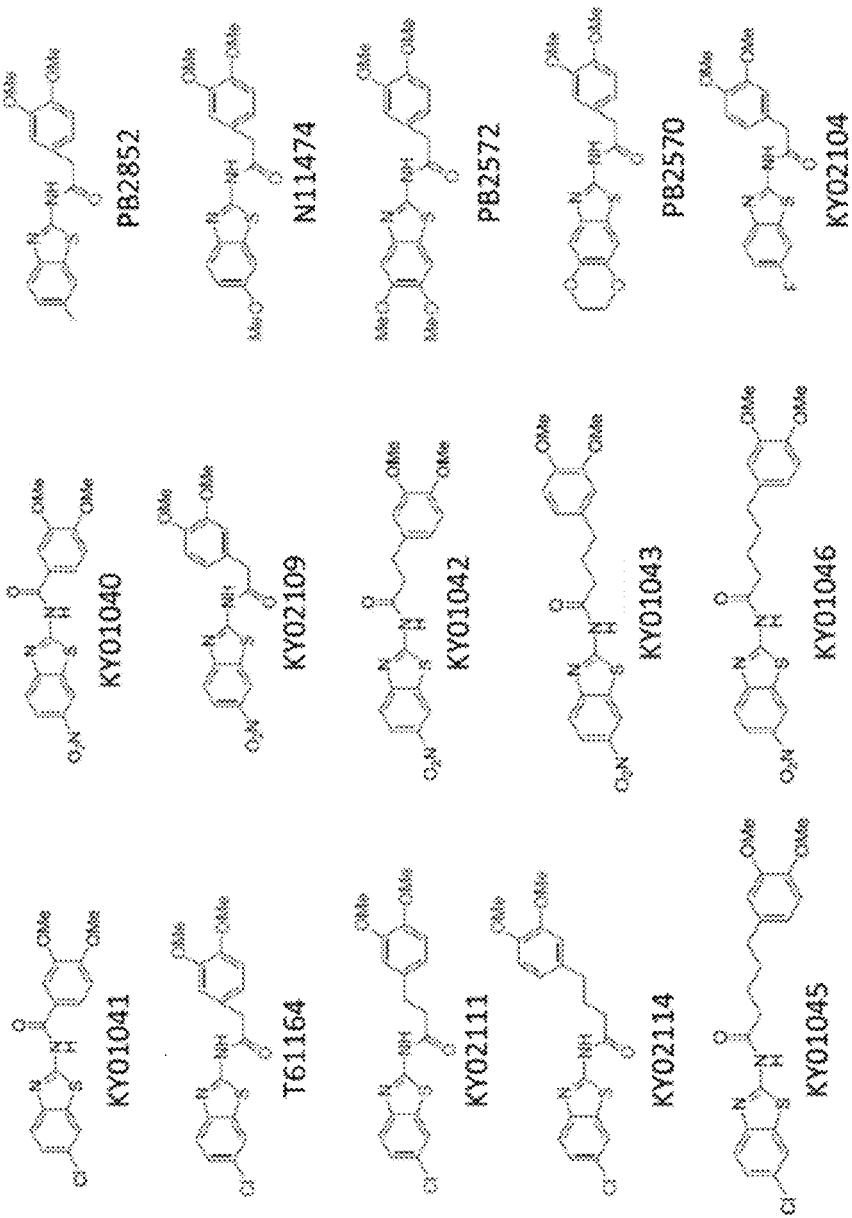
Figures 2, 7:
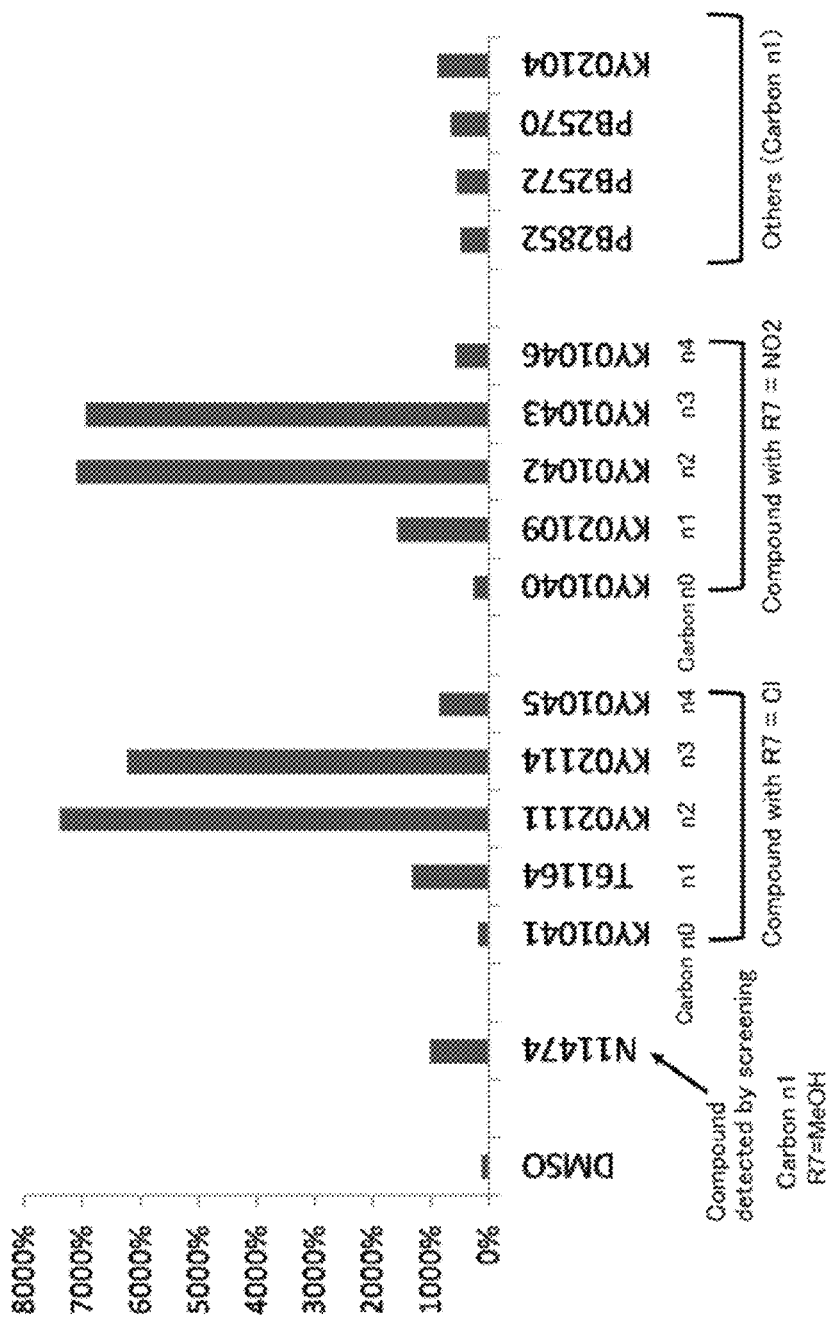
Figure 13:
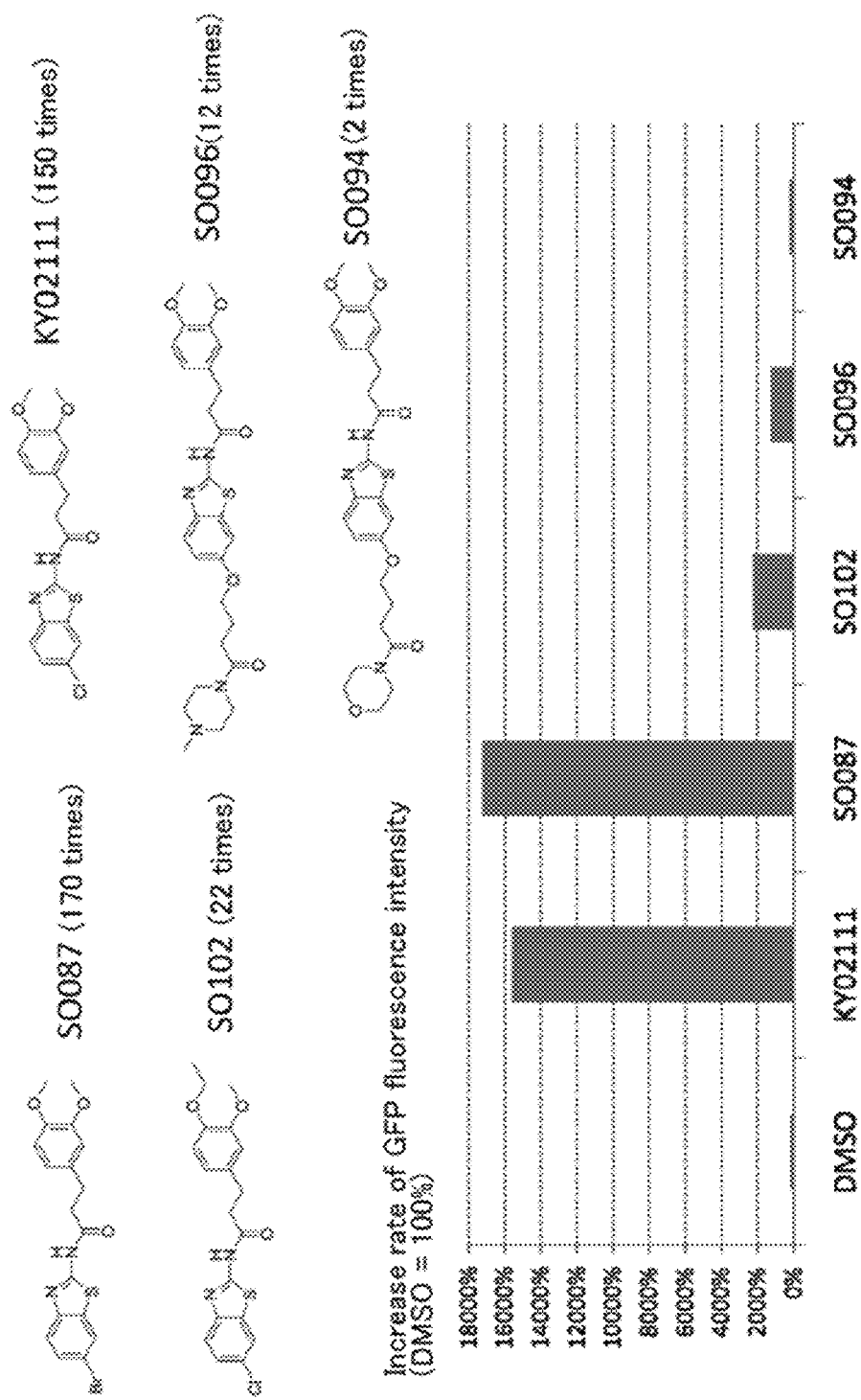
FIG. 13 illustrates compounds which are effective in promoting cardiac muscle cell differentiation (2) and the effect of promoting cardiac muscle cell differentiation of each of the compounds.
Figure 14:
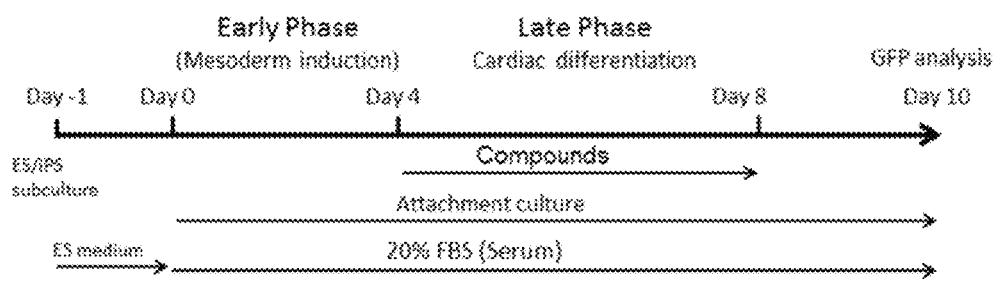
FIG. 14 illustrates a screening strategy of agents which promote cardiac muscle cell differentiation by observing the expression of green fluorescent protein (GFP) under control of promoter of α-MHC gene.

As shown in FIGS. 7 and 13, other analogous compounds were also tested and found to be effective in promoting cardiac muscle cell differentiation.

Example 3

Structure-Activity Relationship of KY02111 Analogues at Position $R_7$

Compounds substituted at the position $R_7$ of Formula 1, which corresponds to Cl of KY02111, were synthesized and examined for the effect of promoting cardiac muscle cell differentiation in a dose-dependent manner in monkey ES cells as described in Example 2. Specifically, a vector expressing green fluorescent protein (GFP) under control of promoter of α-MHC gene, a marker of cardiac muscle cell differentiation, was introduced into monkey ES cells (CMK 6.4 cynomolgus monkey ES cell line) and the cells were seeded on 6-well culture plates (Asahi Glass/5816-006: Ezview culture plate) in 4.0×10⁵ cells/well, and cultured in an IMDM-based differentiation medium for cardiac muscle cells (200 ml IMDM (Sigma) containing 50 ml bovine fetal serum (GIBCO), 2.5 ml MEM non-essential amino acid solution (Sigma), 2.5 ml penicillin-streptomycin (GIBCO), 2.5 ml 200 mM L-glutamine, 2 µl 2-mercaptoethanol). Each compound was added to the cells during day 4 to day 8 of the cardiac muscle cell differentiation culture, and the GFP fluorescence was analyzed at day 10 by using MetaMorph imaging system.

Example 4

The Effect of Promoting Cardiac Muscle Cell Differentiation by Compounds of Example 3

Figure 15:
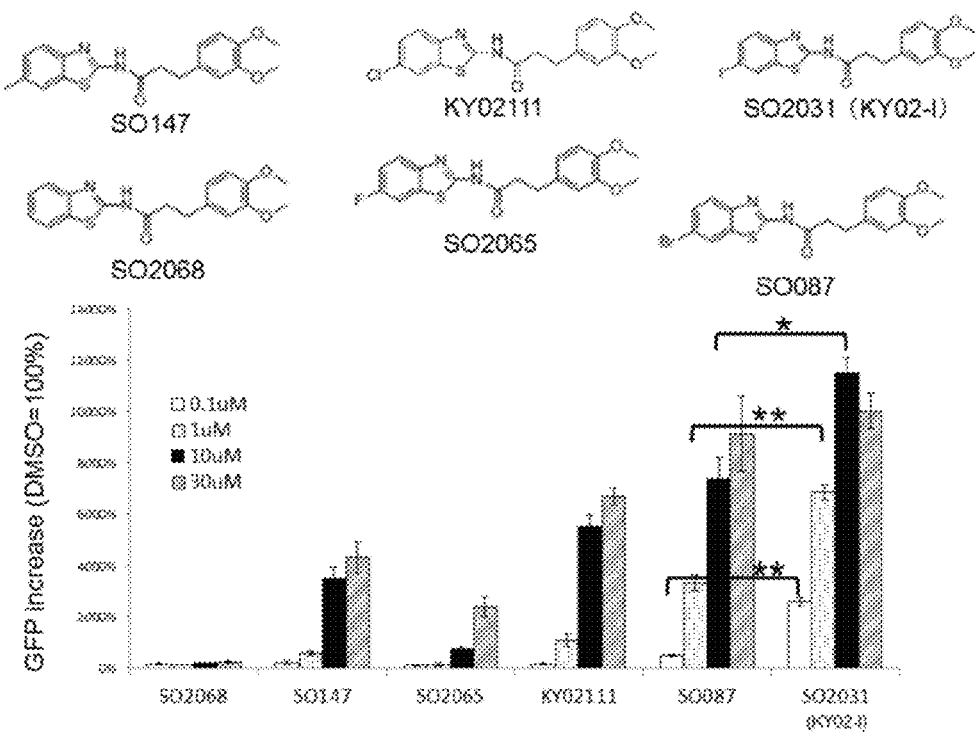
FIG. 15 is a plot of green fluorescent protein (GFP) expression increase (%) as a function of $R_7$ substitutions of KY02111 compound. The effect of promoting cardiac muscle cell differentiation increased in the order of H<F<CH3<Cl<Br<I at $R_7$ position.

As shown in FIG. 15, the effect of promoting cardiac muscle cell differentiation increased in the order of the compounds having H, F, $CH_3$, Cl, Br, and I (H<F<$CH_3$<Cl<Br<I) at $R_7$ position. In particular, SO2031 (referred to as KY02-I hereinafter), which was an iodine substitution analogue, showed the effect about 16, 6.3, 2.1, and 1.5 times higher than that of KY02111 having Cl at $R_7$ position in 0.1 μM, 1 μM, 10 μM, and 30 μM, respectively. Further, SO2031 (KY02-I) showed the effect about 5.2, 2, 1.6, and 1.1 times higher than that of SO087 having Br at $R_7$ position in 0.1 μM, 1 μM, 10 μM, and 30 μM, respectively. Those results demonstrate that the iodine substitution analogue is the most effective especially in a lower dose.

Example 5

Figure 16:
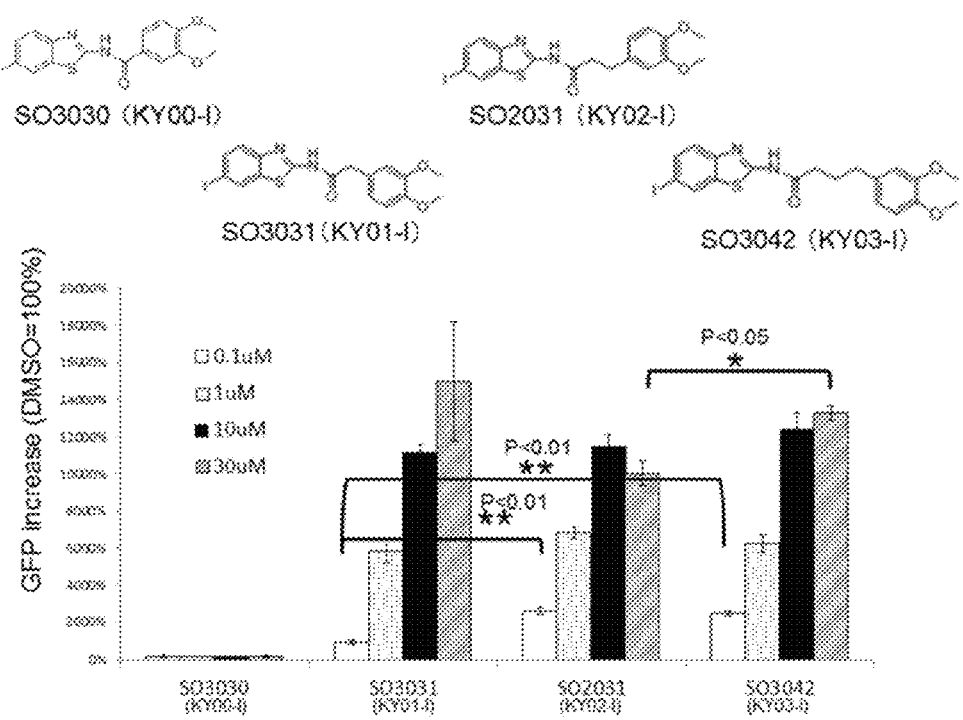
FIG. 16 is a plot of green fluorescent protein (GFP) expression increase (%) as a function of varying carbon chain length (n) in SO2013 (KY02-I).

Structure-Activity Relationship about the Carbon Chain Length of Iodine Substitution Analogues Compounds each having a carbon chain length (n) different from that of KY-02I were synthesized and examined for the effect of promoting cardiac muscle cell differentiation (FIG. 16). As a result, SO3031 (KY01-I) having a carbon chain length of 1, SO2031 (KY02-I) having a carbon chain length of 2, and SO3042 (KY03-I) having a carbon chain length of 3 showed the higher effect compared to KY02111, while SO3030 (KY00-I) having a carbon chain length of 0 showed almost no effect. In addition, at a low dose (0.1 μM), SO2031 (KY02-I) having a carbon chain length of 2 and SO3042 (KY03-I) having a carbon chain length of 3 showed the higher effect compared to SO3031 (KY01-I) having a carbon chain length of 1 (2.7 and 2.8 times, respectively). Further, at a high dose (10 μM or 30 μM), SO3042 (KY03-I) showed the effect slightly higher than that of SO2031 (KY02-I) (1.3 times).

Example 6

Comparison of Iodine Substitution Analogues Having the Carbon Chain Lengths of 2 and 3

The effect of promoting cardiac muscle cell differentiation of SO2031 (KY02-I) having a carbon chain length of 2 and SO3042 (KY03-I) having a carbon chain length of 3 was confirmed in a separate experiment from FIG. 16 in a dose-dependent manner (FIG. 17). As a result, at 0.1 μM, 0.4 μM and 2 μM, those compounds showed a comparable effect, and at a higher dose (10 μM), SO3042 (KY03-I) showed the effect slightly higher than that of SO2031 (KY02-I). Together with the result of FIG. 16, SO3042 (KY03-I) having a carbon chain length n=3 has the effect of promoting cardiac muscle cell differentiation slightly higher than that of SO2031 (KY02-I) at a higher dose.

Example 7

Figure 18:
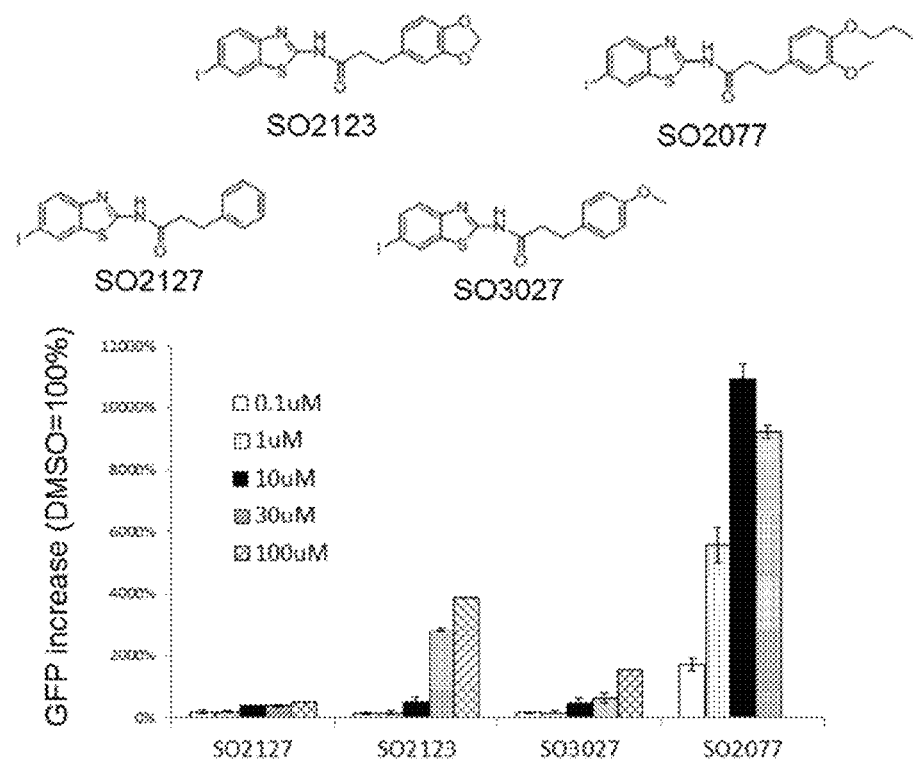
FIG. 18 is a plot of green fluorescent protein (GFP) expression increase (%) for iodine analogues of SO2031 (KY02-I) substituted at $R_2$ and $R_3$ groups. The cardiac muscle cell differentiation was decreased when the compounds had no dimethoxy groups except for SO2077, which showed comparable effect.

Structure-Activity Relationship about $R_2$ and $R_3$ Groups of Iodine Substitution Analogues Compounds having different groups at the positions of the methoxy groups of KY02111, which corresponded to $R_2$ and $R_3$ of Formula I, were synthesized and examined for the effect of promoting cardiac muscle cell differentiation (FIG. 18). As a result, the effect of promoting cardiac muscle cell differentiation was decreased when the compounds had no dimethoxy structure except for SO2077 having a propoxy group at the position $R_2$ instead of a methoxy group. SO2077 showed the effect comparable to SO2031 (KY02-I) having the dimethoxy structure.

Example 8

Figure 19:
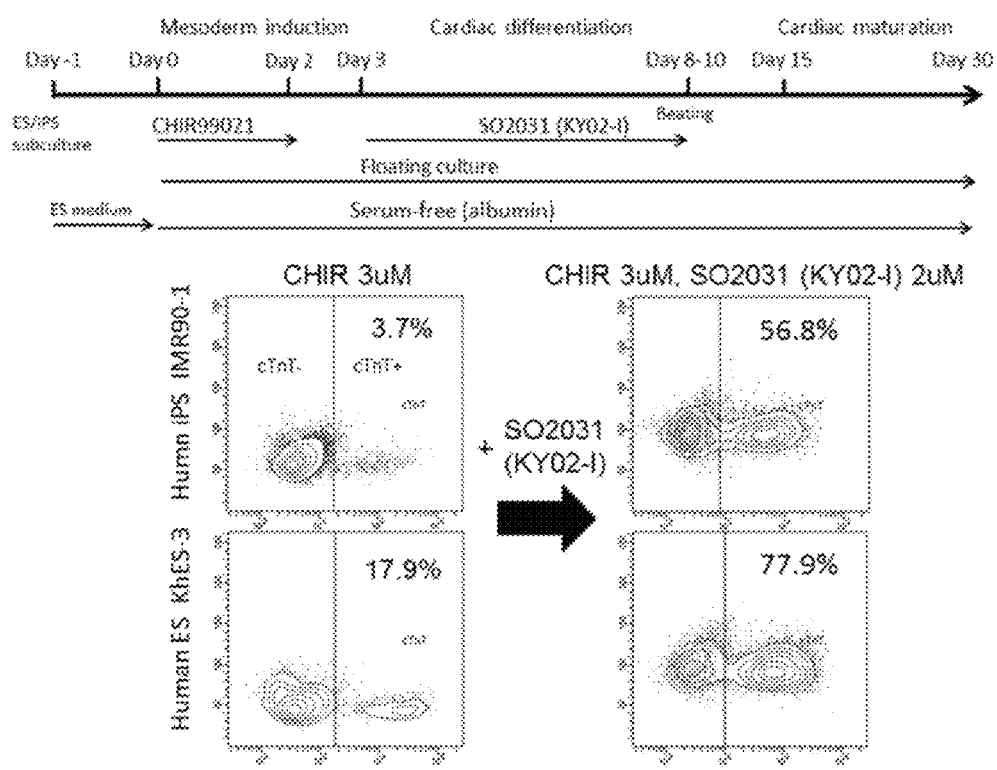
FIG. 19 illustrates the effect of promoting cardiac muscle cell differentiation of the iodine substitution analogue SO2031 (KY02-I) in human ES/iPS cells.

Effect of Promoting Cardiac Muscle Cell Differentiation of the Iodine Substitution Analogue SO2031 (KY02-I) in Human ES/iPS Cells The effect of promoting cardiac muscle cell differentiation of SO2031 (KY02-I) was confirmed using human ES cells (KhES-3) and iPS cells (IMR90-1) (FIG. 19). Induction of cardiac muscle cell differentiation was performed as described previously (Cell Reports, Volume 2, Issue 5, 1448-1460, 25 Oct. 2012). Specifically, IMDM (Sigma) containing 1% MEM non-essential amino acid solution (Sigma), 1% penicillin-streptomycin (Gibco), 2 mM L-glutamine (Sigma), 0.5 mM L-carnitine (Sigma), 0.001% 2-mercaptoethanol (Gibco), and 0.4% human serum albumin (Sigma) was used for culture. Cardiac muscle cell differentiation was induced in Ultra-low attachment culture dish (Corning) by floating culture. During the first two days, 3 μM CHIR99021, a WNT activator, was added, and during days 3-8 of culture, 2 μM SO2031 (KY02-I) was added. Efficiency of cardiac muscle cell differentiation was determined by calculating the percentage of cardiac muscle cells by flow cytometry using an antibody for cardiac troponin T (cTnT), a cardiac-specific marker molecule. As a result, SO2031 (KY02-I) increased the ratio of cardiac muscle cells from 3.7% to 56.8% in human iPS cells (IMR90-1), and from 17.9% to 77.9% in human ES cells (KhES-3). Those results demonstrate that the iodine substitution analogue SO2031 (KY02-I) efficiently promotes cardiac muscle cell differentiation at a lower dose without the stimulation by cytokines and growth factors not only in monkey ES cells but also in human ES/iPS cells.

Example 9

Solubility of the Iodine Substitution Analogue SO2031 (KY02-I) in Medium

Figure 20:
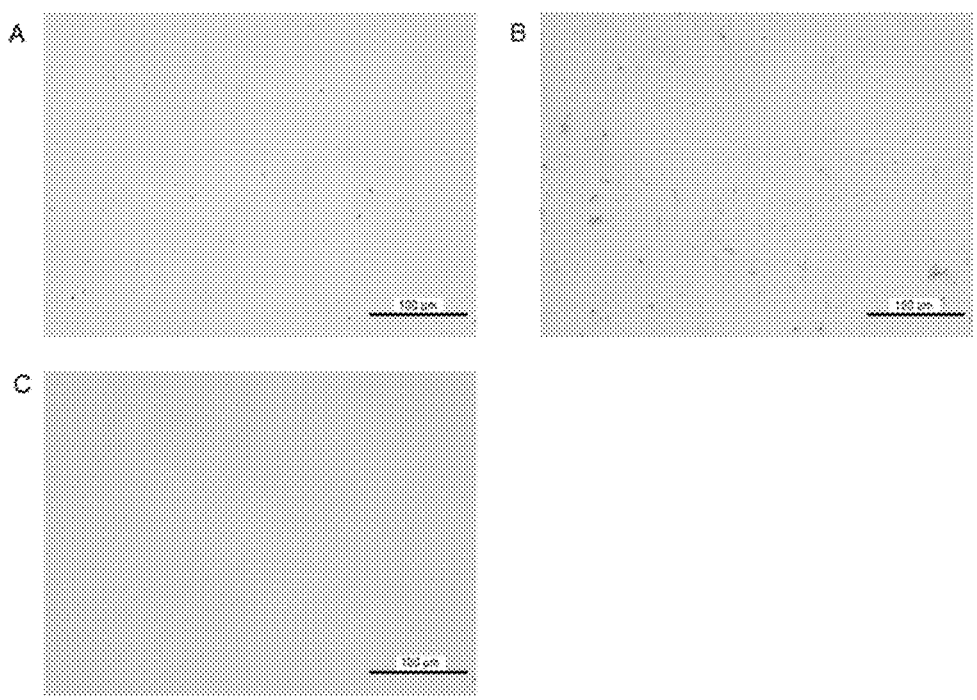
FIGS. 20A-20C are images taken of SO2031 (KY02-I) dissolved in 20% serum-containing medium at 20 μM (A), and in serum-free medium at 3 (B) or 20 μM (C) and observed after 24 hours. Large crystals were not observed in any of the media.

SO2031 (KY02-I) was dissolved in 20% serum-containing medium (200 ml IMDM (Sigma) containing 50 ml bovine fetal serum (GIBCO), 2.5 ml MEM non-essential amino acid solution (Sigma), 2.5 ml penicillin-streptomycin (GIBCO), 2.5 ml 200 mM L-glutamine, 2 μl 2-mercaptoethanol) at 20 μM, and in serum-free medium (200 ml IMDM (Sigma) containing 2.5 ml MEM non-essential amino acid solution (Sigma), 2.5 ml penicillin-streptomycin (GIBCO), 2.5 ml 200 mM L-glutamine, 2 μl 2-mercaptoethanol) at 3 or 20 μM and observed after 24 hours (FIG. 20). Large crystals were not observed in any of the media. Also, in the serum-free medium, almost no crystal was observed at 3 μM, at which concentration a sufficient promotion of cardiac muscle cell differentiation was obtained. As the compound is not crystallized, the concentration of the compound in the medium is stably maintained. Also, there is no possibility that the crystals affect the cells, and there is no risk that the crystals remained in the cells are transferred to and affect the host at transplantation.

Example 10

Figure 4:
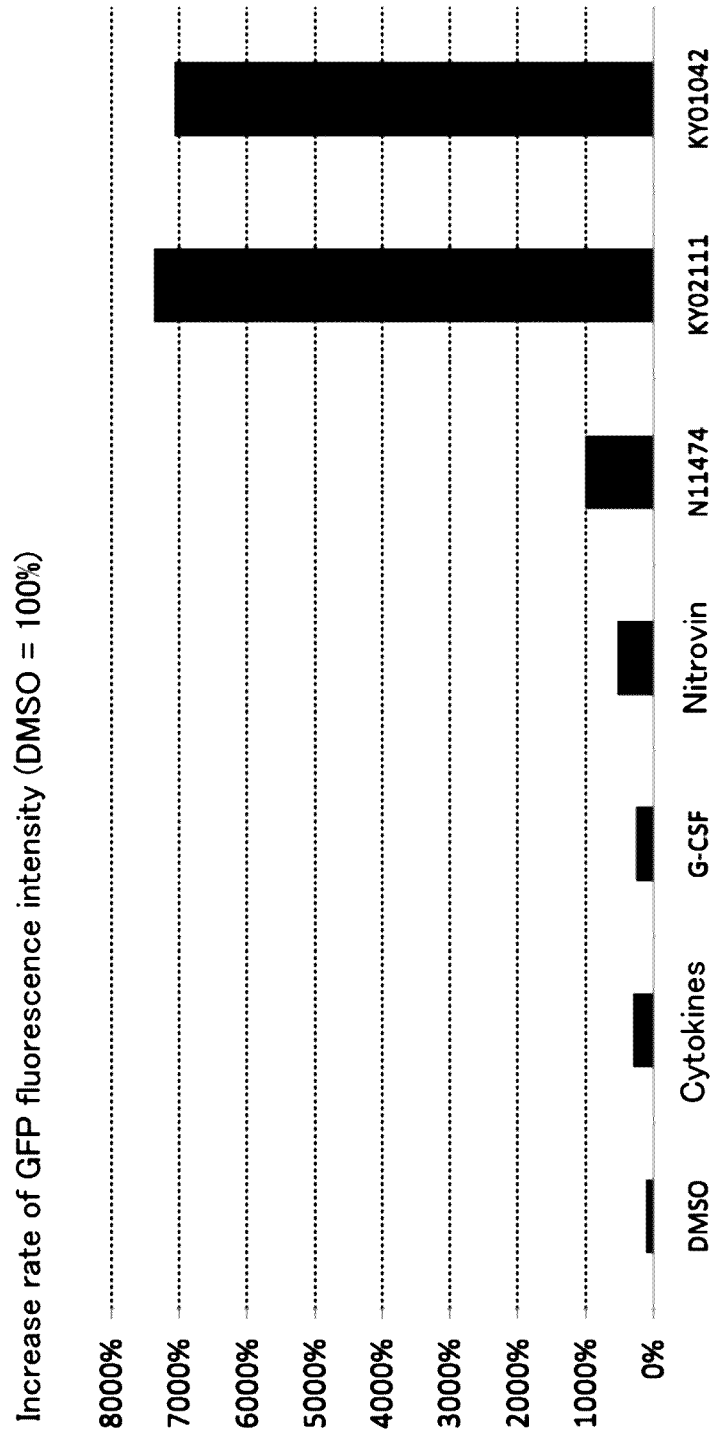
FIG. 4 illustrates the comparison in the effects of promoting cardiac muscle cell differentiation among cytokines, G-CSF, nitrovin, N11474, KY02111 and KY01042.

Cytokines (bFGF, BMP4, VEGF, DKK1, Activin A) known as a cardiac muscle cell differentiation promoter, granulocyte-colony stimulating factor (G-CSF), and nitrovin which was found effective in promoting cardiac muscle cell differentiation by the present inventors were compared with the compounds of the present invention in terms of the effect of promoting cardiac muscle cell differentiation based on the increase of GFP expression level. In the same manner as in the above (2), monkey ES cells were seeded on a 6-well plate, N11474, KY02111, KY01042 (final concentration 10 μM each) and G-CSF (final concentration 5 ng/ml) were added during day 4 to 10 of culture, nitrovin (final concentration 5 μM) was added during day 8 to 14 of culture, and cytokines (bFGF, BMP4, VEGF, DKK1, Activin A) (at respective final concentrations 5 ng/ml, 10 ng/ml, 10 ng/ml, 150 ng/ml and 3 ng/ml) were added during day 1 to 14 of culture, and the GFP expression was observed at day 14 of culture. As a result, N11474, KY02111 and KY01042 showed far higher increases (N11474=1000%, KY02111=7400% and KY01042=7000%) in the GFP expression level than cytokines (about 300%), G-CSF (about 250%) and nitrovin (about 400%) (FIG. 4).

Example 11

Figures 1, 5:
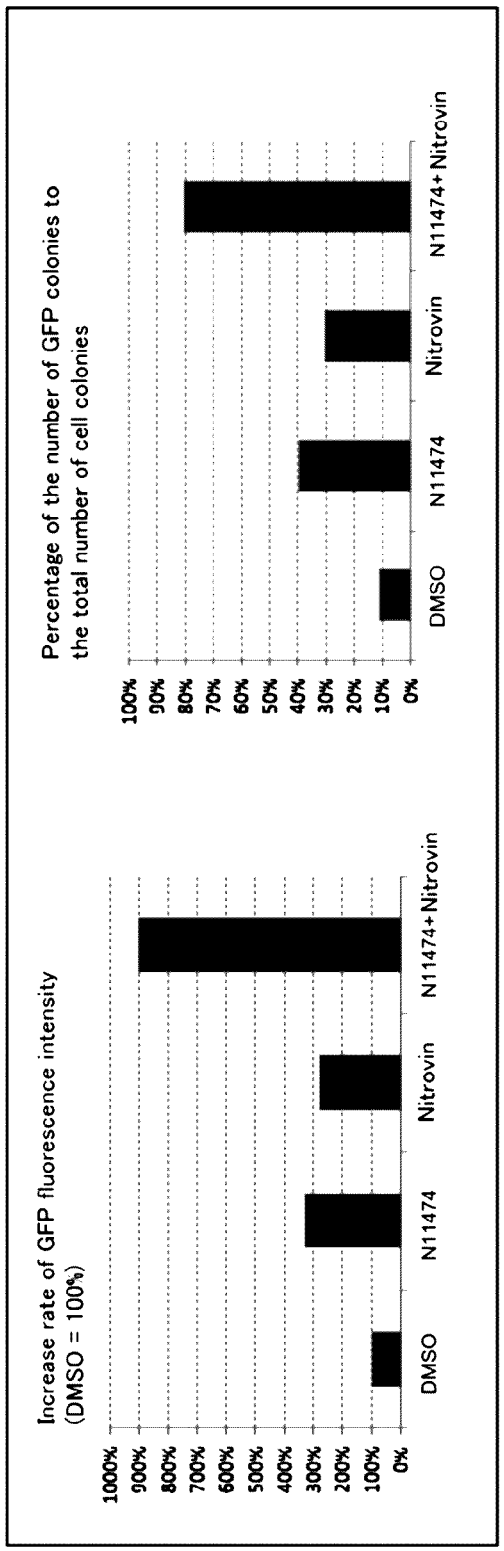
Figures 2, 5:
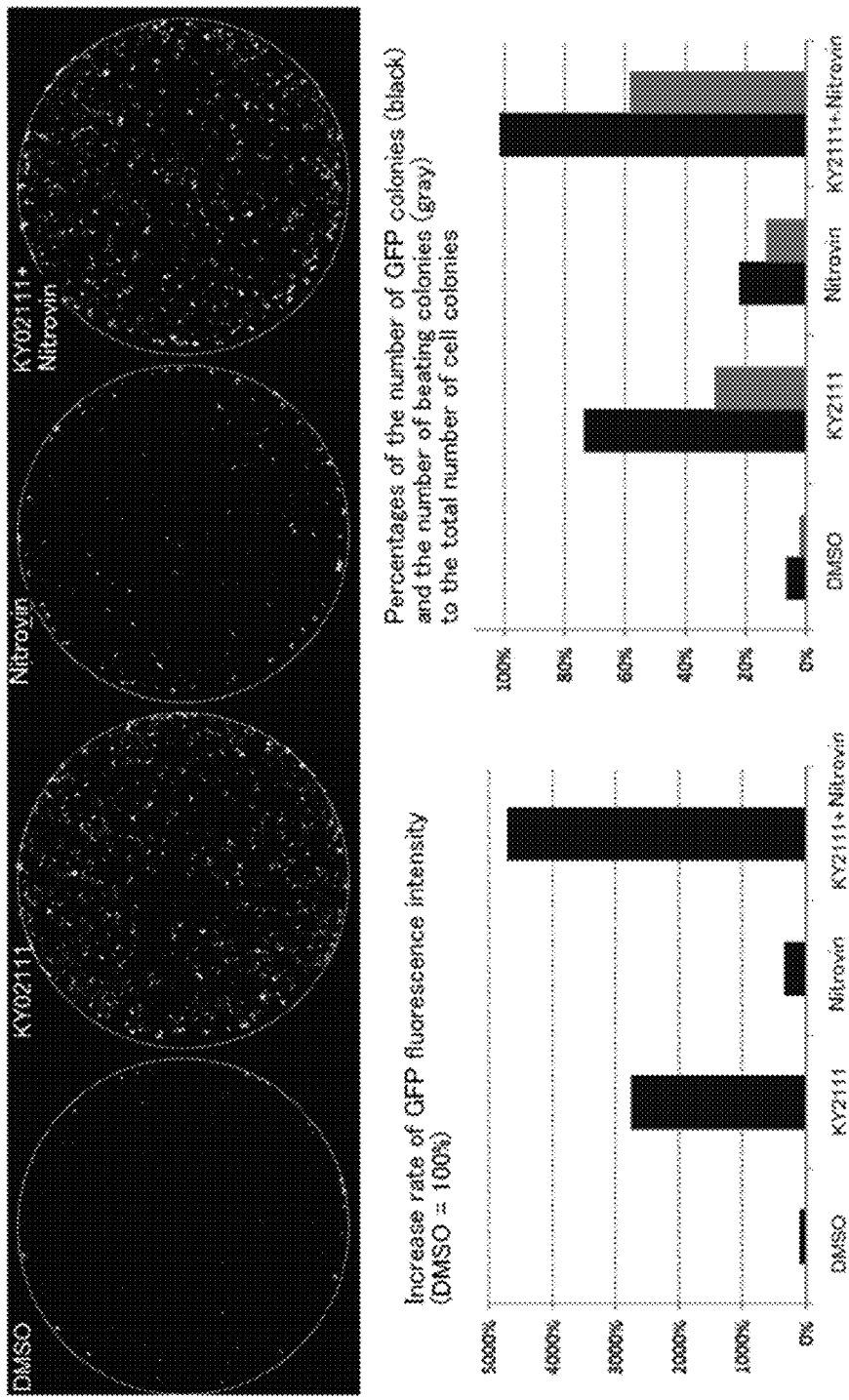

Nitrovin and N11474 were examined for the synergistic effect in the effect of promoting cardiac muscle cell differentiation. N11474 (10 μM) was added during day 4 to 10 of culture and nitrovin (3 μM) was added during day 8 to 14 of culture, and the GFP expression was observed at day 14 of culture. As a result, the increase in the GFP expression level was about 3 to 4 times when nitrovin or N11474 was singly administered, whereas the level increased about 9 times when nitrovin and N11474 were used in combination (FIG. 5-1, left graph). Also, the proportion of the number of GFP colonies increased by an about 30 to 40% when nitrovin or N11474 was singly administered, whereas the proportion increased by about 80% when nitrovin and N11474 were used in combination (FIG. 5-1, right graph).

Similarly, nitrovin and KY02111 were examined for the synergistic effect in the effect of promoting cardiac muscle cell differentiation. KY02111 (5 μM) was added during day 4 to 8 of culture, nitrovin (1 μM) was added during day 8 to 12 of culture, and the GFP expression was observed at day 14 of culture. As a result, the increases in the GFP expression level were respectively about 3 times and about 30 times as much more than Control (DMSO) when nitrovin or KY02111 was singly administered, whereas the level increased about 50 times when nitrovin and KY02111 were used in combination (FIG. 5-2, left graph). Also, the ratios of number of GFP colonies increased respectively by about 22% and 73% when nitrovin or KY02111 was singly administered, whereas all the colonies were substantially (100%) GFP fluorescence positive when nitrovin and KY02111 were used in combination (FIG. 5-2, bottom right graph). Further, the proportions of beating colonies were about 16% and 30% respectively when nitrovin or KY02111 was singly administered, whereas the proportion was 58% when nitrovin and KY02111 were used in combination (FIG. 5-2, bottom right graph).

Example 12

The effect of promoting differentiation of each of the ES/iPS cells into cardiac muscle cells were confirmed for N11474 and KY02111 with the GFP expression level and number of beating colonies used as the indicators. Human ES cell line (Kh-1 line) (Suemori, H., et al., Efficient establishment of human embryonic stem cell lines and long-term maintenance with stable karyotype by enzymatic bulk passage. Biochem Biophys Res Commun. 345(3), 926-32 (2006)) (incorporated herein by reference) was seeded in a 6-well plate (Asahi Glass/5816-006: Ezview culture plate) in 1.2×106 cells/well and cultured for 22 days, with BMP4 (10 ng/ml) added during day 0 to 4 of culture and N11474 (10 μM) or KY02111 (5 μM) added during day 4 to 14 of culture. Human iPS cell lines (253G1, IMR90-1, IMR90-4 and RCHIPC0003) (Takahashi, K., et al., Induction of pluripotent stem cells from adult human fibroblasts by defined factors. Cell. 131(5), 861-72 (2007); Yu, J., et al., Induced pluripotent stem cell lines derived from human somatic cells. Science. 318(5858), 1917-20 (2007)) (these references are herein incorporated by reference) were cultured for the cardiac muscle cell differentiation in the same manner as for the human ES cells. The cardiac muscle cells from mouse ES cells (R1) were differentiated in accordance with the method described in the reference (Transient inhibition of BMP signaling by Noggin induces cardiomyocyte differentiation of mouse embryonic stem cells. Yuasa S, et al. Nat. Biotechnol. 2005 May; 23(5): 607-11; incorporated herein by reference). KY02111 (5 μM) was added for 3 days during day 6 to 9 of cardiac muscle cell differentiation culture and the beating colonies of cardiac muscle cells were analyzed at day 9. Monkey ES cells (CMK6.4) were cultured for cardiac muscle cell differentiation in the same manner as in the above (2).

Figure 6:
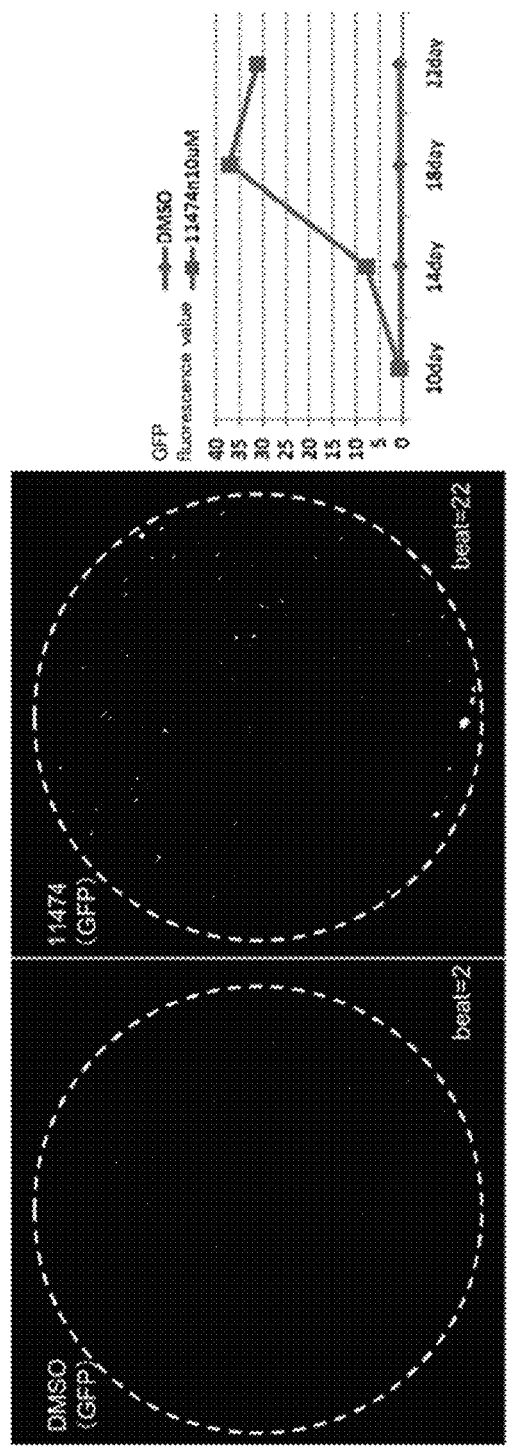
FIG. 6 illustrates the effect of N11474 on human ES cells in promoting cardiac muscle cell differentiation (increase of GFP expression level).

As a result, at day 14 and after of culture, a significant increase in the GFP expression level was observed (FIG. 6). Also, the number of beating colonies increased significantly with the maximum of about 60 times in monkey ES cells (CMK6.4), mouse ES cells (R1), human ES cells (Kh-1) and human iPS cells (253G1, IMR90-1, IMR90-4 and RCHIPC0003) by the administration of N11474 and KY02111 (Table 1). As described above, it was confirmed that these compounds were highly effective in promoting cardiac muscle cell differentiation for human ES cells and iPS cells and mouse ES cells.

TABLE 1

Effect of the compounds for promoting cardiac muscle cell differentiation (N11474, KY02111) on each ES/iPS cell line (Increase rate in the number of beating colonies as compared to the control (DMSO))

| ES/iPS cell line (line name) | Beating cardiac muscle cell differentiation efficiency (Control (DMSO) = 100%) |
|---|---|
| Monkey ES (CMK6.4) | 1850% (KY02111) |
| Human ES (Kh-1) | 1100% (N11474) |
| Mouse ES (R1) | 200% (KY02111) |
| Human iPS (253G1) | 1500% (KY02111) |
| Human iPS (IMR90-1) | 6100% (KY02111) |
| Human iPS (IMR90-4) | 4000% (N11474) |
| Human iPS (RCHIPC0003) | 100% (KY02111) |

Example 13

Figure 8:
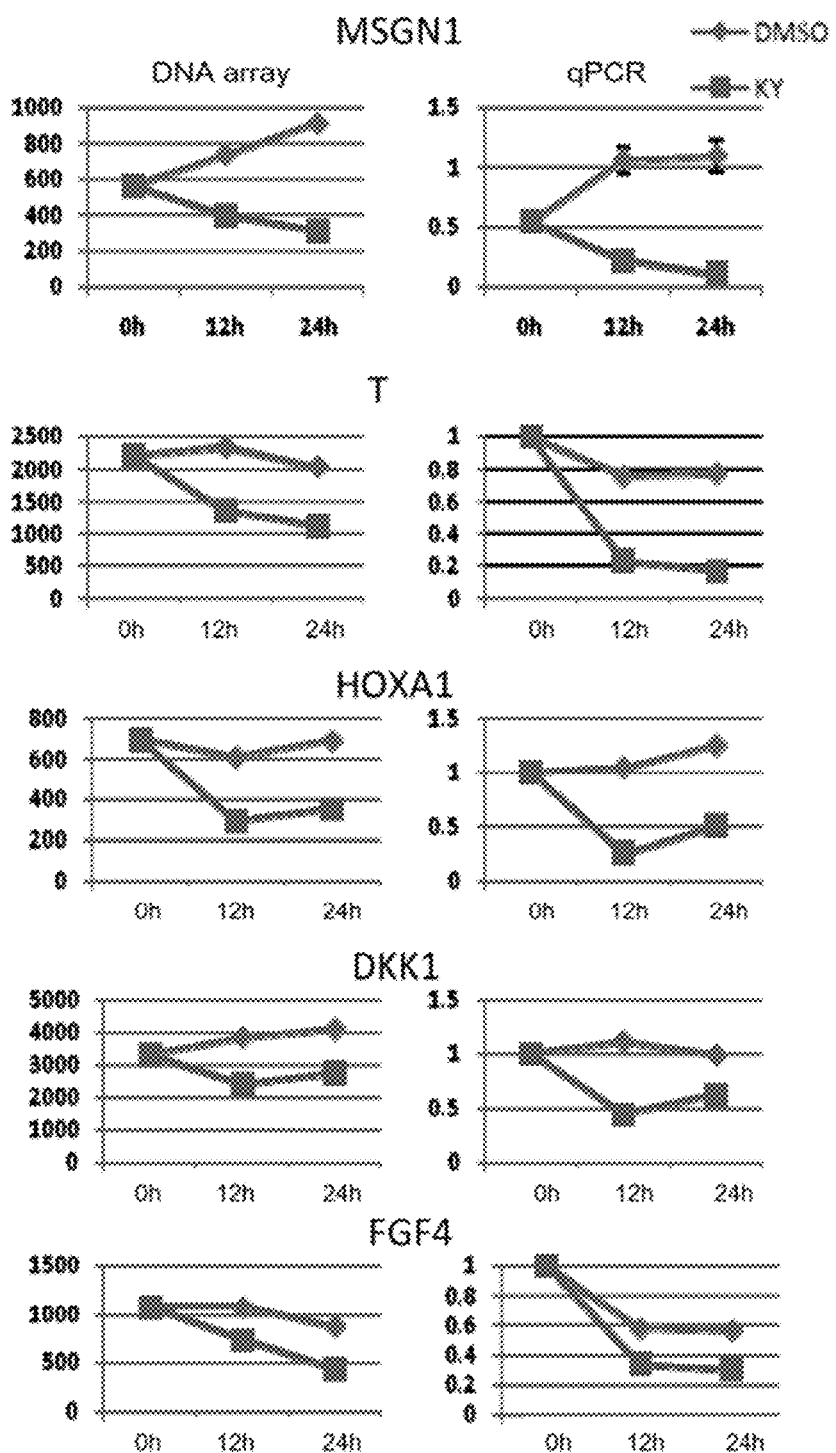
FIG. 8 illustrates the effect of KY02111 on gene expression.

To examine the action mechanism of compounds of the present invention, human iPS cells were seeded in the differentiation medium for cardiac muscle cells described in the above (1), DMSO or KY02111 (10 M) was added at day 3 of culture and the gene expressions 12 hours and 24 hours after the addition were analyzed by the DNA array. As a result, it was revealed that expressions of the following genes were reduced by the addition of KY02111: (in the order of the genes whose expression were reduced most 12 hours later) HOXA1, MSGN1, NKD1, T, TNFRSF11B, DKK1, DKK4, CDX2, MSX1, NODAL, FGF4, PAPPA, PRRX1, LRAT, CYP1B1, SLC34A2, AXIN2, LGL1, SPS, MIXL1, APCDD1 and DSEL. The promoter analysis using the TCF/LEF transcription factor recognition sequence was performed and it was revealed that these genes contained many genes which function at the downstream of the Wnt signaling pathway. A part (MSGN1, HOXA1, T, Dkk1 and FGF4) of these genes was confirmed for the expression by the quantitative polymerase chain reaction (qPCR) and all of these genes had the same results as the DNA array analysis (FIG. 8).

Figures 1, 9:
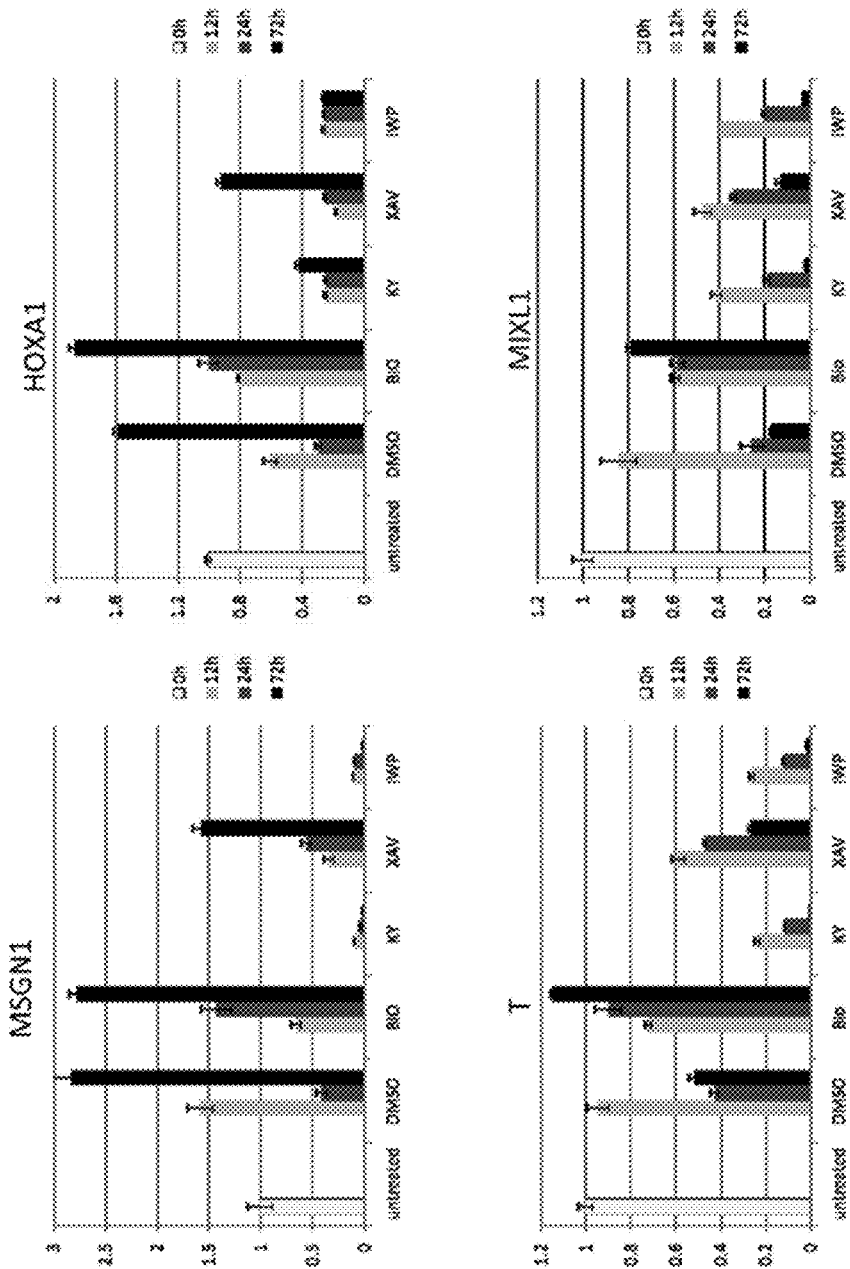

Next, the effects of KY02111, XAV939 and IWP-2, known Wnt signaling inhibitors, and BIO, a Wnt signaling activator, on the group of genes which were found to have reduced expression by the addition of KY02111 were analyzed by the quantitative polymerase chain reaction. The analyzed genes were as follows: MSGN1, HOXA1; T, MIXL1; Dkk1, AXIN2; NODAL and FGF4 (all known as Wnt signaling target genes). As a result, the expressions of these genes were also reduced by any of the compounds KY02111, XAV939 and IWP-2, whereas increased by BIO, the Wnt signaling activator (FIG. 9).

The above results suggest that the group of genes found to have reduced expression by the addition of KY02111 in the DNA array is the genes located at the downstream of the Writ signaling pathway and that KY02111 is a Wnt signaling inhibitor.

Example 14

Figure 10:
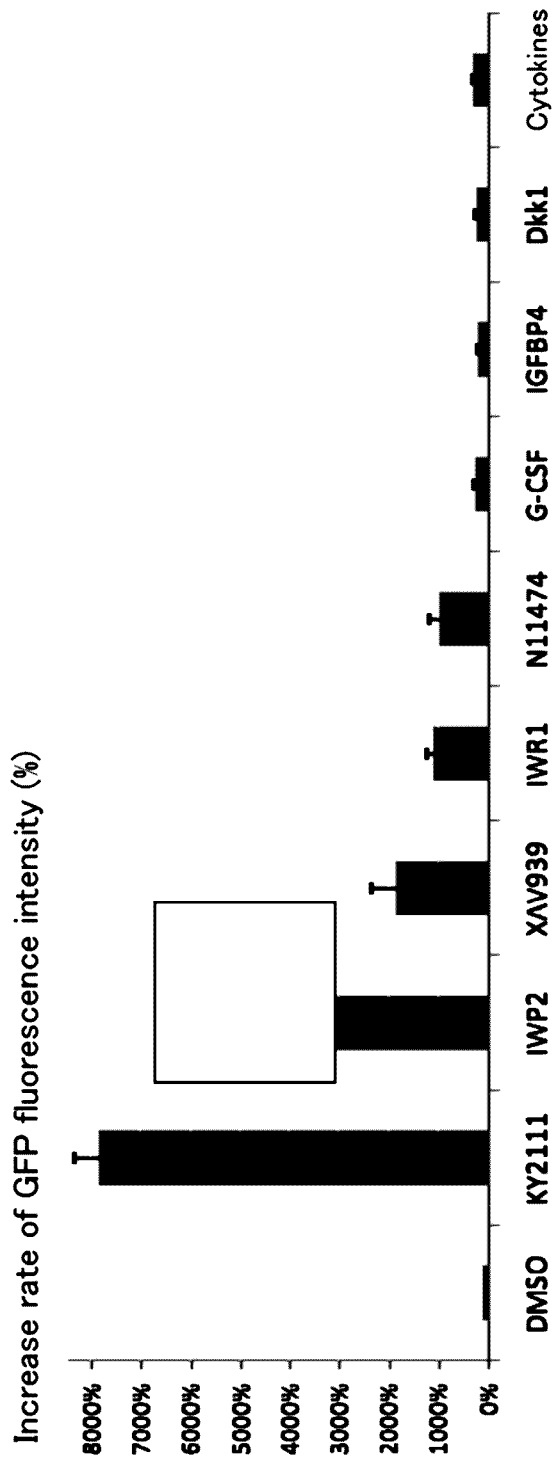
FIG. 10 illustrates the comparison in the effect of promoting cardiac muscle cell differentiation among KY02111, N11474, known Wnt signaling inhibitors (IWP2, XAV939, IWR1) and proteins (G-CSF, IGFBP4, Dkk1 and cytokines) known to have the effect of promoting cardiac muscle cell differentiation.

In the same manner as Example 2, the effects of promoting cardiac muscle cell differentiation were compared among KY02111 and N11474, known Wnt signaling inhibitors (IWP2, XAV939 and IWR1), proteins known to be effective in promoting cardiac muscle cell differentiation (G-CSF, IGFBP4, Dkk1 and cytokines (a mixture of bFGF, BMP4, VEGF, DKK1 and Activin A)). Monkey ES cells were seeded on a 6-well plate, KY02111 and N11474 (final concentration 10 µM each), IWP2 (final concentration 10 µM), XAV939 (final concentration 10 µM), IWR1 (final concentration 10 µM), G-CSF (fmal concentration 5 ng/ml), IGFBP4 (final concentration 1 µg/ml) and Dkk1 (final concentration 150 ng/ml) were added during day 4 to 10 of culture and cytokines (a mixture of bFGF, BMP4, VEGF, DKK1 and Activin A) (at respective final concentrations 5 ng/ml, 10 ng/ml, 10 ng/ml, 150 ng/ml and 3 ng/ml) were added during day 1 to 14 of culture and the GFP expressions were observed at day 14 of culture. As a result, the known Wnt signaling inhibitors also showed the effect of promoting cardiac muscle cell differentiation but KY02111 had the strongest effect of promoting cardiac muscle cell differentiation (FIG. 10).

Example 15

Figure 11:
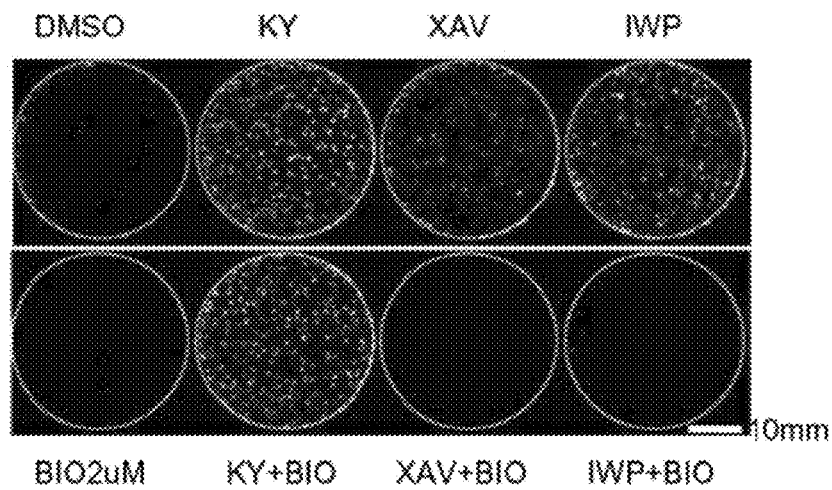
Figure 1:
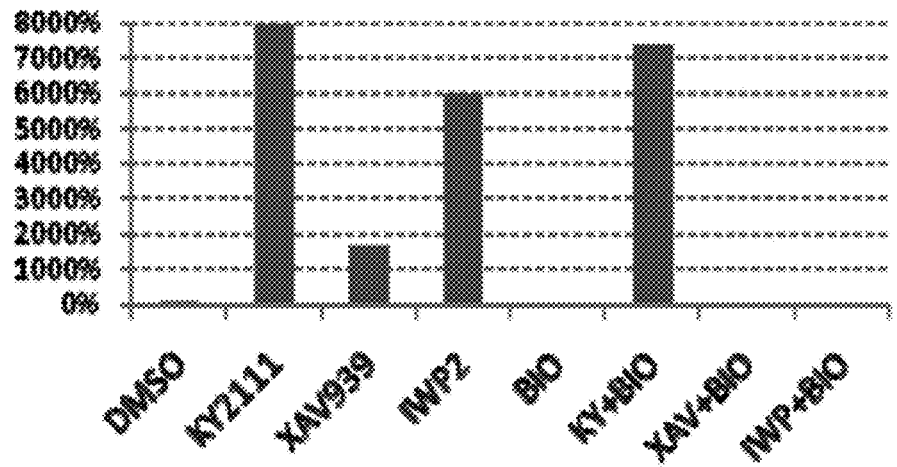
Figures 2, 11:
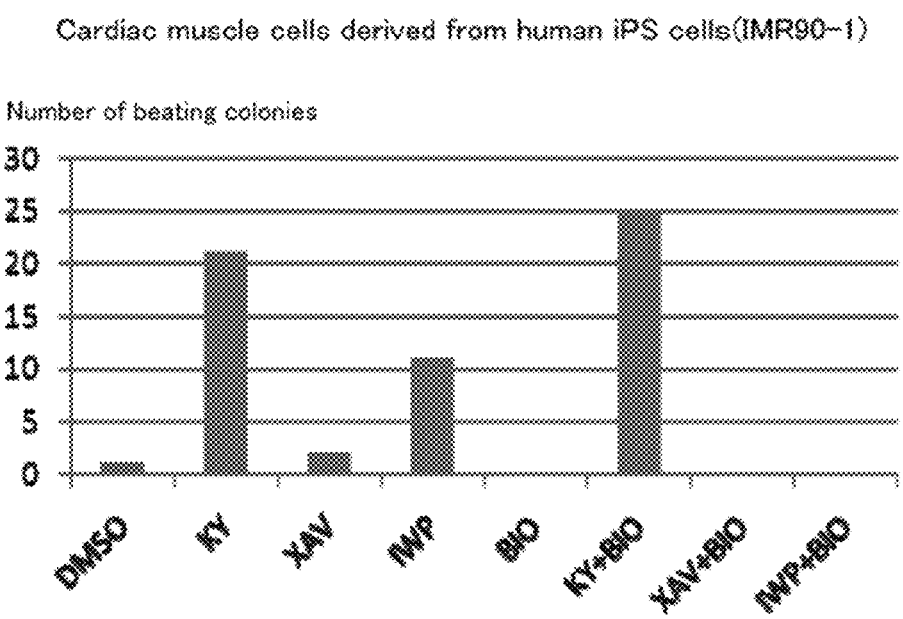

The effect of BIO, a Wnt signaling activator, on the effect of promoting cardiac muscle cell differentiation of KY02111, XAV939 and IWP2 was analyzed. In the same manner as in the above (8), BIO (final concentration 5 µM) was added to the monkey ES cells together with KY02111, XAV939 or IWP2 during day 4 to 10 of culture, and the GFP expression was observed at day 14 of culture. As a result, BIO inhibited the effect of cardiac muscle cell differentiation by XAV939 and IWP2 but did not inhibit the effect by KY02111 (FIG. 11). The same results were found when the number of beating colonies was analyzed using human iPS cells (IMR90-1) as described in the above (5) (FIG. 11). These results suggest that KY02111 has the different action mechanism of the cardiac muscle cell differentiation effect from the known Wnt signaling inhibitors.

Example 16

The synergistic effects between KY02111 and a known Wnt signaling inhibitor XAV939 or IWP2 in the promotion of cardiac muscle cell differentiation were analyzed. In the same manner as in the above (8), KY02111, XAV939 and IWP2 were added to monkey ES cells during day 4 to 10 of culture, and the GFP expression was observed at day 14 of culture. As a result, the synergistic effect was observed between KY02111 and XAV939 (FIG. 12). Also, the number of beating colonies was analyzed using human iPS cells (IMR90-1) as described in the above (8), and the synergistic effects were observed between KY02111 and XAV939 and KY02111 and IWP2 (FIG. 12-2). The above results suggest that KY02111 has a different action mechanism from the known Wnt signaling inhibitors and an even stronger effect of promoting cardiac muscle cell differentiation is achieved when both are used in combination.

Example 17

Synthesis of KY01041

3,4-Dimethoxybenzoylyl chloride (100 mg, 0.55 mmol) and triethylamine (83.0 µl, 6 mmol) were dissolved in methylene chloride (500 µl), 2-amino-6-chlorobenzothiazole (105 mg, 0.57 mmol) was added thereto, and the mixture was stirred for 1 hour at room temperature. After completion of the reaction, the reaction solution was diluted in methylene chloride and washed with a saturated saline solution. The solution was dried over magnesium sulfate and the solvent was evaporated. Ethanol was added to the residue, which was heated to 70° C., dissolved and recrystallized by cooling the temperature to room temperature, thereby obtaining 130 mg of 2-(3,4-dimethoxybenzamide)-6-chlorobenzothiazole in a yield of 68%.

1H NMR (CDCl3): δ10.15 (s, 1H), 7.83 (d, J=1.8 Hz, 1H), 7.63-7.45 (m, 3H), 7.36 (dd, J=1.8, 8.7 Hz, 1H), 6.91 (d, J=8.2 Hz, 1H), 3.96 (s, 3H), 3.94 (s, 3H). MS (ESI) Found: 349 [M+H]+.

Synthesis of KY02111

Using 3-(3,4-dimethoxyphenyl)propanoyl chloride (100 mg, 0.42 mmol) and 2-amino-6-chlorobenzothiazole (78 mg, 0.42 mmol) as substrates, the reaction was performed in the same manner as above, thereby obtaining 113 mg of 2-(3-(3,4-dimethoxyphenyl)propanamide)-6-chlorobenzothiazole in a yield of 72%.

1H NMR (CDCl3): δ9.41 (s, 1H), 7.79 (d, J=2.9 Hz, 1H), 7.62 (d, J=11.7 Hz, 1H), 7.37 (dd, J=2.6, 11.4 Hz, 1H), 6.80-6.67 (m, 3H), 3.85 (s, 3H), 3.82 (s, 3H), 3.03 (t, J=9.9 Hz, 2H), 2.77 (t, J=9.9 Hz, 2H). MS (ESI) Found: 399 [M+H]+.

Synthesis of KY02114

Using 4-(3,4-dimethoxyphenyl)butanoyl chloride (100 mg, 0.41 mmol) and 2-amino-6-chlorobenzothiazole (76 mg, 0.41 mmol) as substrates, the reaction was performed in the same manner as above, thereby obtaining 121 mg of 2-(4-(3,4-dimethoxyphenyl)butanamide)-6-chlorobenzothiazole in a yield of 75%.

1H NMR (CDCl3): δ9.15 (s, 1H), 7.79 (d, J=2.9 Hz, 1H), 7.64 (d, J=11.3 Hz, 1H), 7.39 (dd, J=2.6, 11.4 Hz, 1H), 6.80-6.68 (m, 3H), 3.87 (s, 3H), 3.84 (s, 3H), 2.67 (t, J=9.9 Hz, 2H), 2.48 (t, J=9.9 Hz, 2H), 2.09 (m, 2H). MS (ESI) Found: 413 [M+H]+.

Synthesis of KY01045

Using 5-(3,4-dimethoxyphenyl)pentanoyl chloride (30 mg, 0.13 mmol) and 2-amino-6-chlorobenzothiazole (23 mg, 0.13 mmol) as substrates, the reaction was performed in the same manner as above, thereby obtaining 39 mg of 2-(5-(3,4-dimethoxyphenyl)pentanamide)-6-chlorobenzothiazole in a yield of 75%.

1H NMR (CDCl3): δ8.91 (s, 1H), 7.79 (d, J=8.7 Hz, 1H), 7.66 (d, J=8.7 Hz, 1H), 7.49 (dd, J=2.3, 8.7 Hz, 1H), 6.79 (d, J=7.8 Hz, 1H), 6.71 (d, J=7.8 Hz, 1H) 6.70 (s, 1H), 3.87 (s, 3H), 3.86 (s, 3H), 2.62 (t, J=7.4 Hz, 2H), 2.52 (t, J=7.3 Hz, 2H), 1.80 (m, 2H), 1.72 (m, 2H). MS (ESI) Found: 405 [M+H]+.

Synthesis of KY01040

Using 3,4-dimethoxybenzoylyl chloride (100 mg, 0.5 mmol) and 2-amino-6-nitrobenzothiazole (105 mg, 0.57 mmol) as substrates, the reaction was performed in the same manner as above, thereby obtaining 100 mg of 2-(3,4-dimethoxybenzamide)-6-nitrobenzothiazole in a yield of 56%.

1H NMR (CDCl3): δ10.15 (s, 1H), 8.80 (d, J=2.3 Hz, 1H), 8.31 (dd, J=2.3, 9.2 Hz, 1H), 7.73 (d, J=9.2 Hz, 1H), 7.63-7.47 (m, 2H), 6.95 (d, J=8.7 Hz, 1H), 3.98 (s, 3H), 3.97 (s, 3H). MS (ESI) Found: 360 [M+H]+.

Synthesis of KY02109

Using 2-(3,4-dimethoxyphenyl)acetyl chloride (100 mg, 0.51 mmol) and 2-amino-6-chlorobenzothiazole (94 mg, 0.51 mmol) as substrates, the reaction was performed in the same manner as above, thereby obtaining 153 mg of 2-(2-(3,4-dimethoxyphenyl)acetamide)-6-chlorobenzothiazole in a yield of 83%.

1H NMR (CDCl3): δ8.91 (s, 1H), 8.75 (s, 1H), 8.31 (dd, J=12.1 Hz, 1H), 7.77 (d, J=11.7 Hz, 1H), 7.00-6.70 (m, 3H), 3.92 (s, 3H), 3.90 (s, 3H), 3.86 (s, 2H). MS (ESI) Found: 396 [M+H]+.

Synthesis of KY01042

Using 3-(3,4-dimethoxyphenyl)propanoyl chloride (100 mg, 0.5 mmol) and 2-amino-6-nitrobenzothiazole (105 mg, 0.57 mmol) as substrates, the reaction was performed in the same manner as above, thereby obtaining 138 mg of 2-(3-(3,4-dimethoxyphenyl) propanamide)-6-nitrobenzothiazole in a yield of 71%.

1H NMR (CDCl3): δ9.29 (s, 1H), 8.75 (d, J=1.8 Hz, 1H), 8.31 (dd, J=2.3, 9.2 Hz, 1H), 7.77 (d, J=9.2 Hz, 1H), 6.80 (d, J=8.7 Hz, 1H), 6.75 (d, J=8.7 Hz, 1H), 6.74 (s, 1H), 3.85 (s, 3H), 3.84 (s, 3H), 3.06 (t, J=7.3 Hz, 2H), 2.83 (t, J=7.3 Hz, 2H). MS (ESI) Found: 388 [M+H]+.

Synthesis of KY01043

Using 4-(3,4-dimethoxyphenyl)butanoyl chloride (55 mg, 0.25 mmol) and 2-amino-6-nitrobenzothiazole (50 mg, 0.25 mmol) as substrates, the reaction was performed in the same manner as above, thereby obtaining 65 mg of 2-(4-(3,4-dimethoxyphenyl) butanamide)-6-nitrobenzothiazole in a yield of 66%.

1H NMR (CDCl3): δ8.75 (d, J=2.3 Hz, 1H), 8.29 (dd, J=2.3, 8.7 Hz, 1H), 7.70 (d, J=8.7 Hz, 1H), 6.75 (d, J=8.7 Hz, 1H), 6.67 (s, 1H), 6.66 (d, J=8.7 Hz, 1H), 3.83 (s, 3H), 3.83 (s, 3H), 2.66 (t, J=7.4 Hz, 2H), 2.54 (t, J=7.3 Hz, 2H), 2.11 (m, 2H). MS (ESI) Found: 402 [M+H]+.

Synthesis of KY01046

Using 5-(3,4-dimethoxyphenyl)pentanoyl chloride (30 mg, 0.13 mmol) and 2-amino-6-nitrobenzothiazole (25 mg, 0.13 mmol) as substrates, the reaction was performed in the same manner as above, thereby obtaining 38 mg of 2-(5-(3,4-dimethoxyphenyl)pentanamide)-6-nitrobenzothiazole in a yield of 70%.

1H NMR (CDCl3): δ8.94 (s, 1H), 8.75 (d, J=2.3 Hz, 1H), 8.32 (dd, J=2.3, 9.2 Hz, 1H), 7.81 (d, J=9.2 Hz, 1H), 6.80 (d, J=7.8 Hz, 1H), 6.72 (d, J=7.8 Hz, 1H) 6.71 (s, 1H), 3.88 (s, 3H), 3.86 (s, 3H), 2.63 (t, J=7.4 Hz, 2H), 2.56 (t, J=7.3 Hz, 2H), 1.82 (m, 2H), 1.73 (m, 2H). MS (ESI) Found: 416 [M+H]+.

Synthesis of KY02104

Using 2-(3,4-dimethoxyphenyl)acetyl chloride (100 mg, 0.51 mmol) and 2-amino-6-fluorobenzothiazole (86 mg, 0.51 mmol) as substrates, the reaction was performed in the same manner as above, thereby obtaining 157 mg of 2-(2-(3,4-dimethoxyphenyl)acetamide)-6-fluorobenzothiazole in a yield of 89%.

1H NMR (CDCl3): δ9.14 (s, 1H), 7.64 (dd, J=6.2, 12.1 Hz, 1H), 7.50 (dd, J=3.6, 11.0 Hz, 1H), 7.14 (ddt, J=3.7, 12.1 Hz, 1H), 6.90-6.78 (m, 3H), 3.90 (s, 3H), 3.87 (s, 3H), 3.80 (s, 2H). MS (ESI) Found: 369 [M+H]+.

Synthesis of SO087

An N,N'-dimethylformamide (5 ml) solution containing 2-amino-6-bromobenzothiazole (500 mg, 2.18 mmol), 3-(3,4-dimethoxyphenyl)propionic acid (505 mg, 2.40 mmol), O-(6-chlorobenzotriazol-1-yl)-N,N,N',N'-tetramethyluronium hexafluorophosphate (1.09 g, 2.63 mmol) and N,N'-diisopropylethylamine (419 µl, 2.41 mmol) was stirred overnight at room temperature. After completion of the reaction, the reaction solution was diluted with ethyl acetate and washed with a saturated sodium hydrogen carbonate aqueous solution, distilled water and a saturated sodium chloride aqueous solution. The solution was dried over sodium sulfate and the solvent was then evaporated. The residue was refluxed in ethanol and recrystallized, thereby obtaining 320 mg of 2-(3-(3,4-dimethoxyphenyl)propanamide)-6-bromobenzothiazole in a yield of 35%.

1H NMR (DMSO-d6): δ12.45 (s, 1H), 8.25 (d, J=1.8 Hz, 1H), 7.66 (d, J=8.4 Hz, 1H), 7.56 (dd, J=1.8, 8.4 Hz, 1H), 6.87-6.83 (m, 2H), 6.77-6.73 (m, 1H), 3.71 (s, 3H), 3.70 (s, 3H), 2.88 (t, J=7.0 Hz, 2H), 2.79 (t, J=7.0 Hz, 2H)

Synthesis of SO102

Using 2-amino-6-chlorobenzothiazole (55 mg, 0.298 mmol) and 3-(3,4-dimethoxyphenyl)propionic acid (80 mg, 0.357 mmol) as substrates, the reaction was performed in the same manner as SO087, thereby obtaining 40 mg of N-(6-chlorobenzothiazol-2-yl)-3-(4-ethoxy-3-methoxyphenyl) propanamide in a yield of 34%.

1H NMR (DMSO-d6): δ12.44 (s, 1H), 8.11 (d, J=2.2 Hz, 1H), 7.71 (d, J=8.8 Hz, 1H), 7.44 (dd, J=2.2, 8.8 Hz, 1H), 6.90-6.82 (m, 2H), 6.72 (dd, J=1.8, 7.0 Hz), 3.94 (q, J=7.0 Hz, 2H), 3.72 (s, 3H), 2.91-2.85 (m, 2H), 2.82-2.75 (m, 2H), 1.28 (t, J=7.0 Hz, 3H)

Synthesis of SO094

Sodium hydride (60%) (106 mg, 2.65 mmol) was added while stirring under ice cooling to an N,N'-dimethylformamide (7 ml) solution containing 2-amino-6-hydroxybenzothiazole (400 mg, 2.41 mmol) under an argon atmosphere and stirred for 30 minutes, and then 4-bromoethyl butyrate (521 μl, 3.62 mmol) was added thereto and stirred overnight at room temperature. After completion of the reaction, the reaction solution was diluted with ethyl acetate and washed with a saturated ammonium chloride aqueous solution and a saturated sodium chloride aqueous solution. The solution was dried over sodium sulfate and the solvent was evaporated, thereby obtaining 372 mg of ethyl 4-((2-aminobenzothiazol-6-yl) (oxy)butanoate in a yield of 55%.

An N,N'-dimethylformamide (5 ml) solution containing ethyl 4-((2-aminobenzothiazol-6-yl)oxy)butanoate (372 mg, 1.33 mmol), 3-(3,4-dimethoxyphenyl)propionic acid (335 mg, 1.59 mmol), O-(6-chlorobenzotriazol-1-yl)-N,N,N',N'-tetramethyluronium hexafluorophosphate (659 mg, 1.59 mmol) and N,N'-diisopropylethylamine (278 μl, 1.59 mmol) was stirred overnight at room temperature. After completion of the reaction, the reaction solution was diluted with ethyl acetate and washed with a saturated sodium hydrogen carbonate aqueous solution, distilled water and a saturated sodium chloride aqueous solution. The solution was dried over sodium sulfate and the solvent was evaporated. The residue was refluxed in ethanol and recrystallized, thereby obtaining 447 mg of ethyl 4-((2-(3-(3,4-dimethoxyphenyl) propanamide)benzothiazol-6-yl)oxy)butanoate in a yield of 76%.

5 N NaOH Aqueous solution (378 μl) was added to a 1,4-dioxane solution containing ethyl 4-((2-(3-(3,4-dimethoxyphenyl)propanamide)benzothiazol-6-yl)oxy)butanoate (447 mg, 0.946 mmol) and stirred overnight at room temperature. After completion of the reaction, the reaction solution was condensed and neutralized with 6 N hydrochloric acid under ice cooling. The deposit was collected by vacuum filtration and washed with water, thereby obtaining 271 mg of 4-((2-(3-(3,4-dimethoxyphenyl)propanamide) benzothiazol-6-yl)oxy)butanoic acid in a yield of 64%.

1-Hydroxybenzotriazole (38 mg, 0.248 mmol) and 1-ethyl-3-(3-dimethylaminopropyl)carbodiimide hydrochloride (52 mg, 0.270 mmol) were added to an N,N'-dimethylformamide (1 ml) solution containing 4-((2-(3-(3,4-dimethoxyphenyl)propanamide)benzothiazol-6-yl)oxy) butanoic acid (100 mg, 0.225 mmol) and morpholine (22 μl, 0.248 mmol) and stirred for 2 days at room temperature. After completion of the reaction, the reaction solution was diluted with ethyl acetate and washed with a saturated sodium hydrogen carbonate aqueous solution, distilled water and a saturated sodium chloride aqueous solution. The solution was dried over sodium sulfate and the solvent was evaporated. The residue was refluxed in ethanol and recrystallized, thereby obtaining 50 mg of 3-(3,4-dimethoxyphenyl)-N-(6-(4-morpholino-4-oxobutoxy)benzothiazol-2-yl) propanamide in a yield of 43%.

1H NMR (DMSO-d6): δ12.20 (s, 1H), 7.60 (d, J=8.8 Hz, 1H), 7.55 (d, J=2.6 Hz, 1H), 7.01 (dd, J=2.6, 8.8 Hz, 1H), 6.86-6.83 (m, 2H), 6.75 (dd, J=1.8, 8.1 Hz), 4.03 (t, J=6.2 Hz, 2H), 3.71 (s, 3H), 3.70 (s, 3H), 3.56-3.53 (m, 4H), 3.46-3.42 (m, 4H), 2.87 (t, J=7.0 Hz), 2H), 2.75 (t, J=7.0 Hz, 2H), 2.51-2.46 (m, 2H), 1.96 (t, J=7.0 Hz, 2H)

Synthesis of SO096

Using 4-((2-(3-(3,4-dimethoxyphenyl)propanamide)benzothiazol-6-yl)oxy)butanoic acid (80 mg, 0.180 mmol) and 1-methylpiperazine (21.8 μl, 0.198 mmol) as substrates, the reaction was performed in the same manner as SO094, thereby obtaining 39 mg of 3-(3,4-dimethoxyphenyl)-N-(6-(4-(4-methylpiperazin-1-yl)-4-oxobutoxy)benzothiazol-2-yl)propanamide in a yield of 41%.

1H NMR (DMSO-d6): δ12.20 (br s, 1H), 7.54 (d, J=8.8 Hz, 1H), 7.48 (d, J=2.6 Hz, 1H), 6.96 (dd, J=2.6, 8.8 Hz, 1H), 6.86-6.82 (m, 2H), 6.73 (dd, J=1.8, 8.1 Hz, 1H), 4.01 (t, J=6.2 Hz, 2H), 3.71 (s, 3H), 3.69 (s, 3H), 3.45-3.41 (m, 4H), 2.86 (t, J=7.7 Hz, 2H), 2.70 (t, J=7.7 Hz, 2H), 2.50-2.45 (m, 2H), 2.29-2.20 (m, 4H), 2.15 (s, 3H), 1.94 (t, J=7.0 Hz, 2H)

Synthesis of SO3031 (KY01-I)

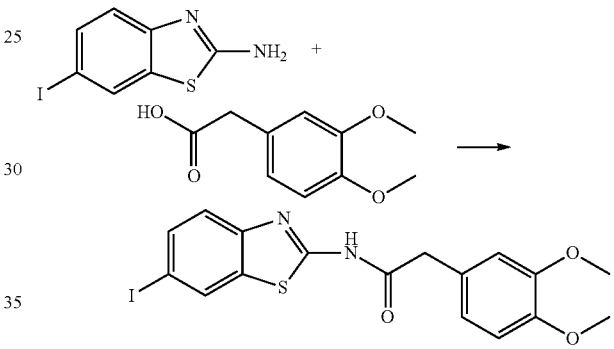

N,N-dimethylformamide solution (3 ml) containing 2-amino-6-iodobenzothiazole (200 mg, 0.723 mmol) and 3,4-dimethoxyphenylacetic acid (157 mg, 0.795 mmol) was added with N,N-diisopropylethylamine (139 μl, 0.803 mmol) and O-(6-chlorobenzotriazol-1-yl)-N,N,N',N'-tetramethyluronium hexafluorophosphate (360 mg, 0.870 mmol) and stirred over night at room temperature. After completion of the reaction, the solution was diluted with ethyl acetate and washed with saturated sodium bicarbonate solution and saturated sodium chloride solution. The solution was dried over anhydrous sodium sulfate and the solvent was removed under reduced pressure. The residue was recrystallized with ethanol and 167 mg of 2-(2-(3,4-dimethoxyphenyl)acetamide)-6-iodobenzothiazole was obtained in a yield of 50%.

$^1$H NMR (DMSO-$d_6$): δ12.61 (s, 1H), 8.37 (s, 1H), 7.73-7.69 (m, 1H), 7.54 (d, J=8.0 Hz, 1H), 6.97-6.84 (m, 3H), 3.75-3.72 (m, 8H). MS (ESI) Found; 455 [M+H]$^+$.

Synthesis of SO2031 (KY02-I)

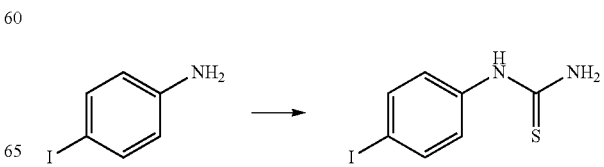

Dichloromethane solution (3 ml) of 4-iodoaniline (1.00 g, 4.57 mmol) was added with thiocarbonyldiimidazole (976 mg, 5.47 mmol) and stirred for 1.5 hours at room temperature. After addition of 25% ammonia solution (3 ml), the solution was stirred over night at room temperature. After completion of reaction, the solvent was removed under reduced pressure, and the resulting deposits were filtered to obtain 889 mg of 1-(4-iodophenyl)thiourea at a yield of 59%

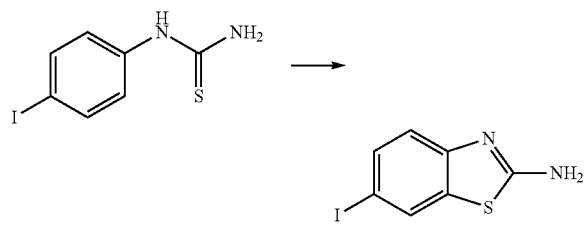

Chloroform suspension (7 ml) of 1-(4-iodophenyl)thiourea (889 mg, 3.19 mmol) was added with bromine (328 μl, 6.40 mmol), and heated to reflux and stirred for 6 hours. After the reaction was completed and the solvent was removed, the residue was added with dichloromethane and washed with saturated sodium bicarbonate solution and saturated sodium chloride solution. After the solution was dried with over anhydrous sodium sulfate and the solvent was removed under reduced pressure, the resulting deposits were filtered to obtain 650 mg 2-amino-6-iodobenzothiazole in a yield of 73%.

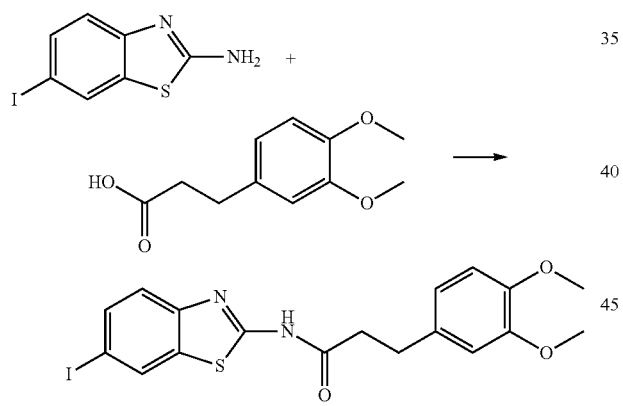

N,N-dimethylformamide solution (2 ml) containing 2-amino-6-iodobenzothiazole (100 mg, 0.362 mmol) and 3-(3,4-dimethoxyphenyl)propionic acid (91.4 mg, 0.435 mmol) was added with N,N-diisopropylethylamine (69.4 μl, 0.398 mmol) and 0-(6-chlorobenzotriazol-1-yl)-N,N,N',N'-tetramethyluronium hexafluorophosphate (180 mg, 0.435 mmol) and stirred over night at room temperature. After completion of the reaction, the solution was diluted with ethyl acetate and washed with saturated sodium bicarbonate solution and saturated sodium chloride solution. The solution was dried over anhydrous sodium sulfate and the solvent was removed under reduced pressure. The residue was recrystallized with ethanol and 83 mg of 2-(3-(3,4-dimethoxyphenyl)propanamid)-6-iodobenzothiazole in a yield of 48%.

$^1$H NMR (DMSO-$d_6$): δ12.42 (s, 1H), 8.37 (s, 1H), 7.72-7.69 (m, 1H), 7.52 (d, J=8.4 Hz, 1H), 6.85-6.83 (m, 2H), 6.75-6.72 (m, 1H), 3.71 (s, 3H), 3.69 (s, 3H), 2.90-2.76 (m, 4H). MS (ESI) Found; 469 [M+H]$^+$.

Synthesis of SO3042 (KY03-I)

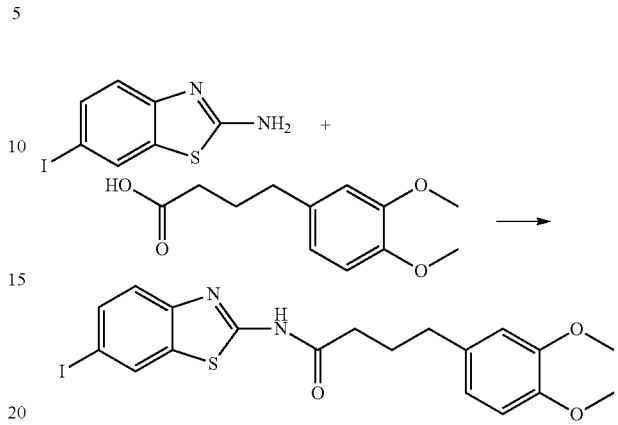

N,N-dimethylformamide solution (3 ml) containing 2-amino-6-iodobenzothiazole (250 mg, 0.905 mmol) and 4-(3,4-dimethoxyphenyl)butanoic acid (224 mg, 0.995 mmol) was added with N,N-diisopropylethylamine (174 μl, 0.995 mmol) and 0-(6-chlorobenzotriazol-1-yl)-N,N,N',N'-tetramethyluronium hexafluorophosphate (450 mg, 1.09 mmol) and stirred over night at room temperature. After completion of the reaction, the solution was diluted with ethyl acetate and washed with saturated sodium bicarbonate solution and saturated sodium chloride solution. The solution was dried over anhydrous sodium sulfate and the solvent was removed under reduced pressure. The residue was recrystallized with ethanol and 131 mg of 2-(4-(3,4-dimethoxyphenyl)butamide)-6-iodobenzothiazole was obtained in a yield of 30%.

$^1$H NMR (DMSO-$d_6$): δ12.37 (s, 1H), 8.37 (s, 1H), 7.72-7.69 (m, 1H), 7.52 (d, J=8.4 Hz, 1H), 6.86-6.79 (m, 2H), 6.70 (d, J=8.0 Hz, 1H), 3.73 (s, 3H), 3.70 (s, 3H), 2.58-2.48 (m, 4H), 1.96-1.86 (m, 2H). MS (ESI) Found; 483 [M+H]$^+$.

Synthesis of SO2077

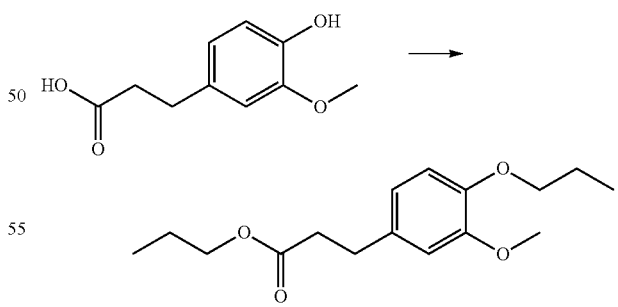

N,N-dimethylformamide solution (5 ml) containing 4-hydroxy-3-methoxypheny propionic acid (500 mg, 2.54 mmol) was added with potassium carbonate (881 mg, 6.37 mmol) and 1-bromopropane (692 μl, 7.65 mmol) and stirred over night at room temperature. After completion of the reaction, the solution was diluted with ethyl acetate and washed with water and saturated sodium chloride solution. The solution was dried over anhydrous sodium sulfate and the solvent was removed under reduced pressure. The residue was purified by silica gel column chromatography (n-hexane/ethyl acetate=4/1) and 590 mg of propyl 3-(3-methoxy-4-propoxyphenyl)propanoate was obtained in a yield of 82%.

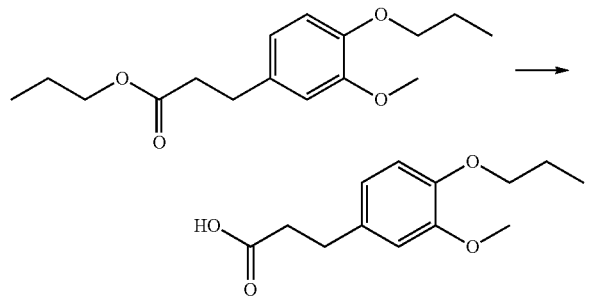

Propyl 3-(3-methoxy-4-propoxyphenyl)propanoate (590 mg, 2.10 mmol) was dissolved in 1,4-dioxane and added with 5 mol/l sodium hydroxide aqueous solution (1.68 ml) and the resulting solution was stirred over night at room temperature. After completion of the reaction, the solution was added with 6 mol/l hydrochloric acid and extracted with ethyl acetate. The organic layer was washed with saturated sodium chloride solution and dried over anhydrous sodium sulfate. The solvent was removed under reduced pressure and 438 mg of 3-(3-methoxy-4-propoxyphenyl)propionic acid was obtained in a yield of 87%.

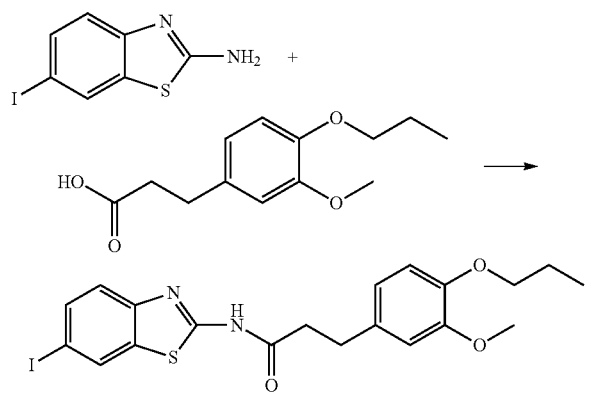

N,N-dimethylformamide solution (3 ml) containing 2-amino-6-iodobenzothiazole (200 mg, 0.723 mmol) and 3-(3-methoxy-4-propoxyphenyl)propionic acid (200 mg, 0.839 mmol) was added with N,N-diisopropylethylamine (140 μl, 0.803 mmol) and O-(6-chlorobenzotriazol-1-yl)-N,N,N',N'-tetramethyluronium hexafluorophosphate (360 mg, 0.870 mmol) and stirred over night at room temperature. After completion of the reaction, the solution was diluted with ethyl acetate and washed with saturated sodium bicarbonate solution and saturated sodium chloride solution. The solution was dried over anhydrous sodium sulfate and the solvent was removed under reduced pressure. The residue was recrystallized with ethanol and 217 mg of 2-(3-(3-methoxy-4-propoxyphenyl)propanamid)-6-iodobenzothiazole was obtained in a yield of 60%.

$^1$H NMR (DMSO-d$_6$): δ12.42 (s, 1H), 8.38-8.37 (m, 1H), 7.72-7.69 (m, 1H), 7.54-7.51 (m, 1H), 6.85-6.82 (m, 2H), 6.72 (d, J=8.0 Hz, 1H), 3.86-3.82 (m, 2H), 3.72 (s, 3H), 2.87-2.78 (m, 4H), 1.72-1.65 (m, 2H), 094 (t, J=7.3 Hz, 3H). MS (ESI) Found; 497 [M+H]$^+$.

All publications and patents mentioned in the above specification are herein incorporated by reference in their entireties. Various modifications and variations of the described nanomaterials and methods will be apparent to those skilled in the art without departing from the scope and spirit of the invention. Although the disclosure has been described in connection with specific preferred embodiments, it should be understood that the invention as claimed should not be unduly limited to such specific embodiments. Indeed, those skilled in the art will recognize, or be able to ascertain using the teaching herein and no more than routine experimentation, many equivalents to the specific embodiments of the invention described herein. Such equivalents are intended to be encompassed by the following claims.

The invention claimed is:

1. A compound or a salt thereof represented by formula,

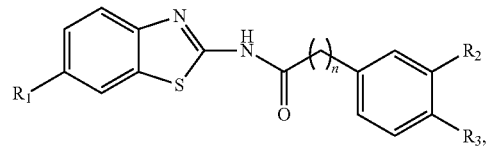

wherein

R$_1$ is I,

R$_2$ and R$_3$ are each independently selected from a methoxy, an ethoxy, or a propoxy, and n is an integer of 1 to 4.

2. The compound or salt thereof according to claim 1, wherein R$_2$ is a methoxy.

3. A compound or salt thereof represented by the following formulae:

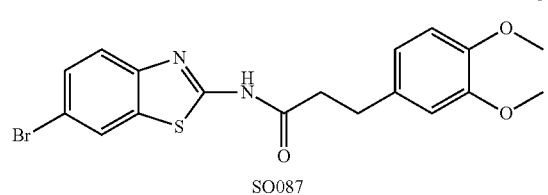

SO087

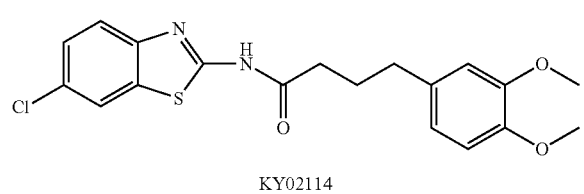

KY02114

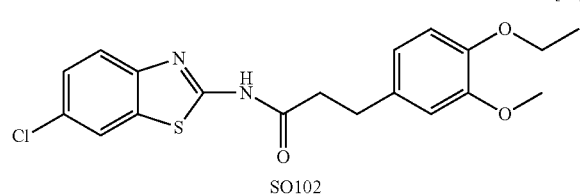

SO102

-continued
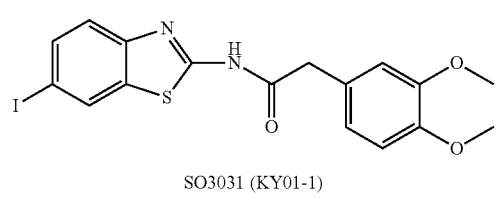
SO3031 (KY01-1)  [21]
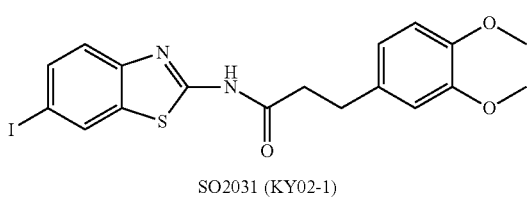
SO2031 (KY02-1)  [22]
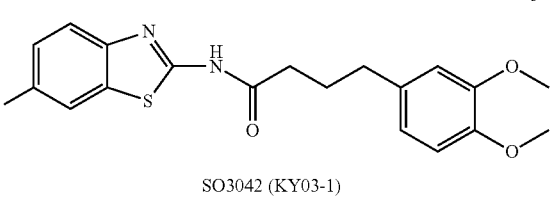
SO3042 (KY03-1)  [23]
or
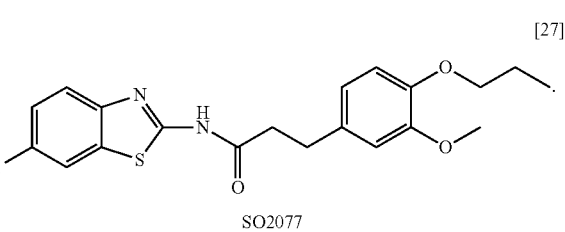
SO2077  [27]
4. The compound or salt thereof according to claim 1, which is
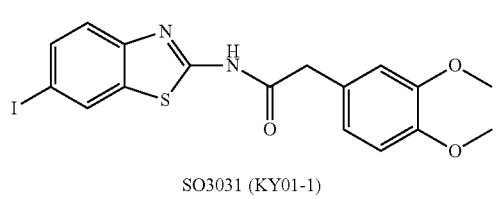
SO3031 (KY01-1)  [21]
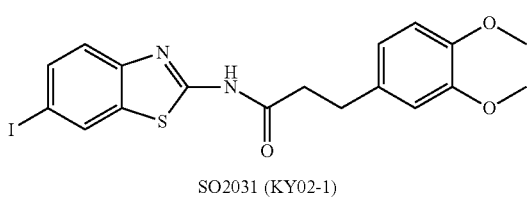
SO2031 (KY02-1)  [22]
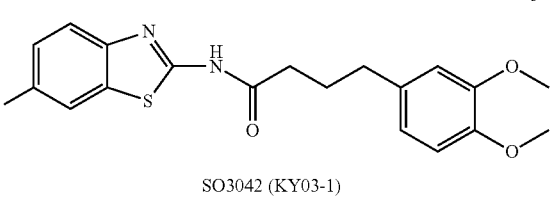
SO3042 (KY03-1)  [23]
or
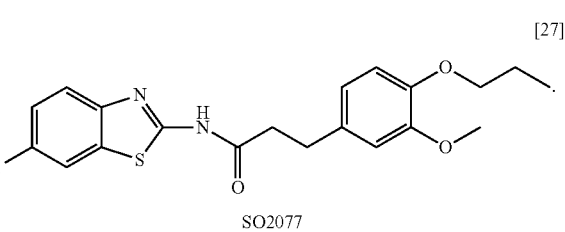
SO2077  [27]
* * * * *